United States Patent
Hunt et al.

(10) Patent No.: US 10,640,535 B2
(45) Date of Patent: May 5, 2020

(54) IDENTIFICATION OF MHC CLASS I PHOSPHO-PEPTIDE ANTIGENS FROM BREAST CANCER UTILIZING SHLA TECHNOLOGY AND COMPLEMENTARY ENRICHMENT STRATEGIES

(71) Applicants: Agenus Inc., Lexington, MA (US); The Board of Regents of the University of Oklahoma, Norman, OK (US)

(72) Inventors: Donald F. Hunt, Charlottesville, VA (US); Andrew Norris, Palmyra, VA (US); Ann Michelle English, Palmyra, VA (US); Jeffrey Shabanowitz, Charlottesville, VA (US); William H. Hilderbrand, Edmond, OK (US); Oriana E. Hawkins, Tuscola, TX (US)

(73) Assignees: AGENUS INC., Lexington, MA (US); THE BOARD OF REGENTS OF THE UNIVERSITY OF OKLAHOMA, Norman, OK (US)

( * ) Notice: Subject to any disclaimer, the term of this patent is extended or adjusted under 35 U.S.C. 154(b) by 89 days.

(21) Appl. No.: 14/403,350

(22) PCT Filed: May 28, 2013

(86) PCT No.: PCT/US2013/042908
§ 371 (c)(1),
(2) Date: Mar. 12, 2015

(87) PCT Pub. No.: WO2013/177593
PCT Pub. Date: Nov. 28, 2013

(65) Prior Publication Data
US 2015/0225456 A1 Aug. 13, 2015

Related U.S. Application Data

(60) Provisional application No. 61/652,028, filed on May 25, 2012, provisional application No. 61/667,697, filed on Jul. 3, 2012.

(51) Int. Cl.
| | | |
|---|---|---|
| C07K 7/08 | (2006.01) | |
| C07K 14/47 | (2006.01) | |
| A61K 39/00 | (2006.01) | |
| C07K 7/06 | (2006.01) | |
| C07K 16/18 | (2006.01) | |
| A61K 38/00 | (2006.01) | |

(52) U.S. Cl.
CPC ............ C07K 7/08 (2013.01); A61K 39/0011 (2013.01); C07K 7/06 (2013.01); C07K 14/4748 (2013.01); C07K 16/18 (2013.01); *A61K 38/00* (2013.01); *C07K 2317/24* (2013.01); *C07K 2317/55* (2013.01)

(58) Field of Classification Search
None
See application file for complete search history.

(56) References Cited

U.S. PATENT DOCUMENTS

| | | |
|---|---|---|
| 6,309,863 B1 | 10/2001 | Anderson et al. |
| 7,166,573 B1 | 1/2007 | Obata |
| 8,124,741 B2 | 2/2012 | Raitano et al. |
| 2004/0086506 A1 | 5/2004 | Haynes et al. |
| 2005/0277161 A1 | 12/2005 | Engelhard et al. |
| 2006/0204509 A1 | 9/2006 | Harty et al. |
| 2006/0251666 A1 | 11/2006 | Nakatsura et al. |
| 2008/0292647 A1 | 11/2008 | Kawakami et al. |
| 2011/0293637 A1 | 12/2011 | Hacohen et al. |
| 2011/0318380 A1 | 12/2011 | Brix et al. |
| 2012/0021432 A1 | 1/2012 | Yu et al. |
| 2012/0129776 A1 | 5/2012 | Cohen et al. |
| 2012/0177669 A1 | 7/2012 | Topalian et al. |
| 2015/0224182 A1 | 8/2015 | Hunt et al. |

FOREIGN PATENT DOCUMENTS

| | | |
|---|---|---|
| WO | WO 1996/040789 | 12/1996 |
| WO | 1999/043829 A2 | 9/1999 |
| WO | WO 2000/073801 | 12/2000 |
| WO | 2003/074675 A2 | 9/2003 |
| WO | 2004/067023 A2 | 8/2004 |
| WO | WO 2009/134883 A1 | 11/2009 |
| WO | WO 2010/129537 | 11/2010 |
| WO | WO 2011/149909 A2 | 1/2011 |
| WO | WO 2014/039675 | 3/2014 |

OTHER PUBLICATIONS

Hara, E., et al., The EMBO Journal, 16(2): 332-342, 1997.*
Andersen et al. Induction of Systemic CTL Responses in Melanoma Patients by Dendritic Cell Vaccination: Cessation of CTL Responses is Associated with Disease Progression. Int. J. Cancer, vol. 94 pp. 820-824 (2001).
Bins et al. Phase I clinical study with multiple peptide vaccines in combination with tetanus toxoid and GMCSF in advanced-stage HLA-A*0201-positive melanoma patients. J. Immunther. 30(2):234-9 (2007).
Bullock et al. "Manipulation of avidity to improve effectiveness of adoptively transferred CD8(+) T cells for melanoma immunotherapy in human MHC class I-transgenic mice," J Immunol 167:5824-5831 (2001).
Bystryn et al. "Double-blind trial of a polyvalent, shed-antigen, melanoma vaccine" Clin Cancer Res 7:1882-1887 (2001).
Chianese-Bullock et al. "Multi-peptide vaccines vialed as peptide mixtures can be stable reagents for use in peptide-based immune therapies" Vaccine 27:1764-1770 (2009).

(Continued)

*Primary Examiner* — Nelson B Moseley, II
(74) *Attorney, Agent, or Firm* — Latrhop GPM LLP; Andrew T. Wilkins; Rebecca L. Wright

(57) ABSTRACT

The present invention describes novel tumor-specific phosphorylated peptides, nucleic acids encoding those peptides, and antibodies generated against said peptides. The genes, peptides, and antibodies described herein may be used as diagnostic indicators of the presence of breast cancer and/or used in therapeutics to treat breast cancer.

55 Claims, 10 Drawing Sheets

Specification includes a Sequence Listing.

(56) References Cited

OTHER PUBLICATIONS

Cobbold et al. Adoptive transfer of cytomegalovirus-specific CTL to stem cell transplant patients after selection by HLA-peptide tetramers. J Exp Med 202:379-386 (2005).
Cottine, J., et al., "Identification of Novel Class I MHC-Restricted Phosphopeptides for Use as Cancer Immunotherapeutics," 58th Annual ASMS Conference on Mass Spectrometry and Allied Topics, Presentation, May 23-27, 2010, Salt Lake City, Utah.
Depontieu et al. (2009) Identification of tumor-associated, MHC class II-restricted phosphopeptides as targets for immunotherapy. Proc Natl Acad Sci U S A 106:12073-12078.
Depontieu et al. (2009) Supplemental Information for "Identification of tumor-associated, MHC class II-restricted phosphopeptides as targets for immunotherapy." Proc Natl Acad Sci U S A 106. DOI:10.1073/pnas.0903852106 (7 pages).
Engelhard, "Identification of phosphorylated peptide antigens displayed on cancer cells and prospects for their use as immunotherapeutics," Powerpoint Presentation, Eleventh international conference on progress vaccination against cancer (PIVAC-11), Oct. 10-13, 2011, Copenhagen, Denmark.
Engelhard, "The contributions of mass spectrometry to understanding of immune recognition by T lymphocytes," Int J Mass Spectrom 259:32-39 (2007).
Evans, A.M., et al., "Differential Comparison of Phosphorylated MHC Class I HLA-A2.1 Peptides from Three Different Cancer Call Lines," Poster, 50th Annual ASMS Conference on Mass Spectrometry and Allied Topics, Jun. 2-6, 2002, Orlando, Florida.
Ferguson et al. "Strategies and challenges in eliciting immunity to melanoma," Immunol Rev 222:28-42 (2008).
Ficarro, S. B., et al., "Identification of Phosphorylated Peptides Associated with Class I MHC Molecules and Implications for Immunotherapy," Poster, 48th Annual ASMS Conference on Mass Spectrometry and Allied Topics, Jun. 11-15, 2000, Long Beach, California.
Goldman et al. "The cancer vaccine roller coaster," Nat Biotechnol 27:129-139 (2009).
Hida et al. A simple culture protocol to detect peptide-specific cytotoxic T lymphocyte precursors in the circulation. Cancer Immunol Immunother 51:219-228 (2002).
Hogan et al. The peptide recognized by HLA-A68.2-restricted, squamous cell carcinoma of the lungspecific cytotoxic T lymphocytes is derived from a mutated elongation factor 2 gene. Cancer Res 58:5144-5150 (1998).
Hopkins, L.M., "Sequence analysis of HLA-B7 peptides by ETD mass spectrometry: Comparative analysis of phosphopeptides on cancer and non-cancer cells," Poster, 53rd Annual ASMS Conference on Mass Spectrometry and Allied Topics, Jun. 5-9, 2005, San Antonio, Texas.
Hunt et al. "Characterization of peptides bound to the class I MHC molecule HLA-A2.1 by mass spectrometry," Science 255:1261-1263 (1992).
James, P.F., et al., "Analysis of HLA-A2 MHC Phosphopeptides with Titanium Dioxide, IMAC, Peptide Derivatization and Electron Transfer Dissociation," Poster, 58th Annual ASMS Conference on Mass Spectrometry and Allied Topics, May 23-27, 2010, Salt Lake City, Utah.
Kielhorn et al. Tissue microarray-based analysis shows phospho-beta-catenin expression in malignant melanoma is associated with poor outcome. Int J Cancer 103:652-656 (2003).
Mackensen et al. "Phase I study in melanoma patients of a vaccine with peptide-pulsed dendritic cells generated in vitro from CD34(+) hematopoietic progenitor cells," Int J Cancer 86:385-392 (2000).
Mohammed, et al. "Phosphorylation-dependent interation between antigenic peptides and MHC class I: a molecular basis for presentation of transformed self," Nat. Immunol., Nov. 2008, vol. 9, No. 11, pp. 1236-1243.
Norris, A., et al., "The Identification of MHC Class II Peptides Expressed in vivo by B-Cell Leukemias and Lymphomas," Poster, 56th Annual ASMS Conference on Mass Spectrometry and Allied Topics, Jun. 1-8, 2008, Denver, Colorado.
Ostankovitch et al. "N-glycosylation enhances presentation of a MHC class I-restricted epitope from tyrosinase," J Immunol 182:4830-4835 (2009).
Petersen et al. Phosphorylated self-peptides alter human leukocyte antigen class I-restricted antigen presentation and generate tumor-specific epitopes. Proc Natl Acad Sci U S A 106:2776-2781 (2009).
Polefrone, J.M., et al., "Differential Expression of Class I, HLA-A2 Phosphopeptides on Tumor Cells: Characterization of Potential Candidates for Immunotherapy or a Cancer Vaccine," Poster, 53rd Annual ASMS Conference on Mass Spectrometry and Allied Topics, Jun. 5-9, 2005, San Antonio, Texas.
Qian, J., et al., "Analysis of HLA-DR4 restricted peptides by electron transfer dissociation tandem mass spectrometry, " Poster, 54th Annual ASMS Conference on Mass Spectrometry and Allied Topics, May 28-Jun. 1, 2006, Seattle, Washington.
Qian, J., et al., "Class I and II MHC restricted phosphopeptides as cancer immunotherapeutics or diagnostics," Poster, 55th Annual ASMS Conference on Mass Spectrometry and Allied Topics, Jun. 3-7, 2007, Indianapolis, Indiana.
Schwartzentruber et al. "gp100 peptide vaccine and interleukin-2 in patients with advanced melanoma," N Engl J Med 364:2119-2127 (2011).
Slingluff "Immunity to melanoma antigens: from self-tolerance to immunotherapy," Adv Immunol 90:243-295 (2006).
Slingluff "Peptide approaches to melanoma vaccines: innovations and challenges," iSTBc/CVC workshop, Alexandria, VA (2005).
Slingluff "The present and future of peptide vaccines for cancer: single or multiple, long or short, alone or in combination?" Cancer J 17:343-350 (2011).
Slingluff et al. "Clinical and immunologic results of a randomized phase II trial of vaccination using four melanoma peptides either administered in granulocyte-macrophage colony-stimulating factor in adjuvant or pulsed on dendritic cells," J Clin Oncol 21:4016-4026 (2003).
Slingluff et al. Randomized multicenter trial of the effects of melanoma-associated helper peptides and cyclophosphamide on the immunogenicity of a multipeptide melanoma vaccine. J Clin Oncol 29(21):2924-2932 (2011).
Tyagi et al. "MAGRIT: the largest-ever phase III lung cancer trial aims to establish a novel tumor-specific approach to therapy," Clin Lung Cancer 10:371-374 (2009).
Utz et al. Proteins phosphorylated during stress-induced apoptosis are common targets for autoantibody production in patients with systemic lupus erythematosus. J Exp Med 185:843-854 (1997).
Wang "Extensive crosstalk between O-GlcNAcylation and phosphorylation regulates cytokinesis," Sci Signal 3:ra2 (2010).
Hojlund et al., "In vivo phosphoproteome of human skeletal muscle revealed by phosphopeptide enrichment and HPLC-ESI-MS/MS," J Proteome Res., 8(11):4954-4965 (2009).
Hung et al., "Cul4A is an oncogene in malignant pleural mesothelioma," J. Cell Mol Med., 15(2):350-8 (2011).
Jia et al., "SCF E3 ubiquitin ligases as anticancer targets," Curr Cancer Drug Targets, 11(3):347-56 (2011).
Lee et al., "Pathogenic Role of the CRL4 Ubiquitin Ligase in Human Disease," Front Oncol., 2:21:1-7, (2012).
Liu et al., "CUL4A abrogation augments DNA damage response and protection against skin carcinogenesis," Mol Cell, 34(4):451-60 (2009).
Ren et al., "Oncogenic CUL4A determines the response to thalidomide treatment in prostate cancer," J Mol Med (Berl), 90(10):1121-32 (2012).
Zarling et al., "Abstract 1584: MHC-restricted phosphopeptides as broad-based immunotherapeutic targets for cancer," Poster Presentations—Tumor Vaccine Development, Proceedings: AACR 103rd Annual Meeting 2012—Mar. 31-Apr. 4, 2012; Chicago, IL, Cancer Research, 72(8):Supplement 1 (2012).
Zarling et al., "Identification of class I MHC associated phosphopeptides as targets for cancer immunotherapy," Proceedings of the National Academy of Sciences of the United States (PNAS), 103:40:14889-14894 (2006).
"CUL4A Antibody" Cell Signaling Technology, Inc. Sep. 16, 2010. <http://www.cellsignal.com/pdf/2699.pdf>.

(56) References Cited

OTHER PUBLICATIONS

International Search Report and the Written Opinion for Int' Appl. No. PCT/US2013/042908, dated Jan. 21, 2014.

Rock and Goldberg, "Degradation of Cell Proteins and the Generation of MHC Class I—Presented Peptides," *Annu Rev Immunol*, 17:739-779 (1999).

Watts, C., "Capture and Processing of Exogenous Antigens for Presentation on MHC Molecules," *Annu Rev Immunol*, 15:821-850 (1997).

Castelli et al., "T-Cell Recognition of Melanoma-Associated Antigens," *J Cell Physiol*, 182:323-331 (2000).

Zarling et al., "Phosphorylated Peptides Are Naturally Processed and Presented by Major Histocompatability Complex Class I Molecules in Vivo," *J. Exp. Med.*, 192:1755-1762 (2000).

Hawkins, O. E. et al., "Identification of Breast Cancer Peptide Epitopes Presented by HLA-A*0201," *Journal of Proteome Research*, 7:1445-1457 (2008).

Altschul S.F. et al., "Basic Local Alignment Search Tool," *Journal of Molecular Biology*, 215:403-410, (1990).

The UniProt Consortium, The Universal Protein Resource (UniProt) in 2010, Nucleic Acids Research, 15:D142-D148 (2010).

Norris A., et al., "Identification of MHC Class I Phospho-peptide Antigens from Breast Cancer Utilizing sHLA Technology and Complementary Enrichment Strategies," Poster presented at 58th ASMS Conference held May 23-27, 2010.

Norris, A. et al, "Utilizing secreted MHC molecules (sHLA) to investigate the phosphor-immuno-peptide of breast cancer," Poster presented at 57th ASMS Conference held May 31-Jun. 4, 2009.

Cobbold et al. (2008) "Immune Targeting of the Phosphoproteome in Hematolymphoid Malignancy," Poster Presented In; The 10th International Conference on Malignant Lymphoma, Jun. 4-7, 2008. Lugano, Switzerland.

Uniprot Database [Online] (Oct. 23, 2007) "UniProtKB—Q6IMB1 (RSLBA_MOUSE)," Accesion No. Q6IMB1. Accessible on the Internet at URL: http://www.uniprot.org/uniprot/Q6IMB1. [Last Accessed Oct. 28, 2016].

\* cited by examiner

TABLE 1

Phosphopeptides Presented on Breast Cancer by the Class I MHC Molecule, HLA B*0702

Breast Cancer Cell Lines: 184B5 (A), BT20 (B) and MCF7 (C)

| # | Sequence | Start | Stop | A/B/C | UniProt | |
|---|---|---|---|---|---|---|
| 70 | APRKGsFSALM | 5 | 14 | A/B | Q13619 | Cullin-4A |
| 71 | ALDsGASLLHL | 482 | 492 | A | P57078 | Receptor-interacting serine/threonine-protein kinase 4 |
| 72 | APLARASsL | 249 | 257 | A | Q15477 | Helicase SKI2W |
| 73 | APRAPsASPLAL | 479 | 490 | A | Q8N3F8 | MICAL-like protein 1 |
| 74 | APRKGsFSAL | 5 | 14 | A/B | Q13619 | Cullin-4A |
| 75 | APSVRsLSL | 278 | 286 | A/B | Q9Y446 | Plakophilin-3 |
| 76 | APSVRSLsL | 278 | 286 | A/B | Q9Y446 | Plakophilin-3 |
| 77 | FPHsLLSVI | 662 | 670 | B | Q9H9Y6 | DNA-directed RNA polymerase I 135 kDa polypeptides/POLR1B |
| 78 | GPRPGsPSAL | 266 | 275 | A/B | Q91Z73 | RNA Pseudouridylate synthase domain |
| 79 | GPRsPPVTL | 147 | 155 | B | Q15735 | Phosphatidylinositol 4,5-bisphosphate 5-phosphatase A |
| 80 | GRtGLPDL | 271 | 278 | A | P55036 | 26S Proteasome non-ATPase regulatory subunit 4 |
| 81 | HPKRSVsL | 160 | 167 | A | O60238 | BCL2/adenovirus E1B 19 kDa protein-interacting protein 3-like |
| 82 | HPRsPNVLSV | 684 | 693 | A | Q16665 | Hypoxia-inducible factor 1-alpha |
| 83 | HPRsPTPTL | 341 | 349 | A | P02812 | Basic salivary proline rich protein 2 |
| 84 | KAFsPVRSV | 2 | 10 | A | Q02363 | DNA-binding protein inhibitor ID-2 |
| 85 | KARsPGRAL | 6 | 14 | A | Q14767 | Latent transforming growth factor-beta-binding protein-2 |
| 86 | KPEsRRSsLL | 428 | 437 | A | Q6WKZ4 | Rab11 family-interacting protein 1 |
| 87 | KPLIRSQsL | 217 | 225 | A/B/C | Q9H6H4 | Receptor expression-enhancing protein 4 |
| 88 | KPRPPPLsP | 328 | 336 | A/B | Q15162 | Cdc42-interacting protein 4 |
| 89 | KPRsPDHVL | 859 | 867 | A | Q9UPN3 | Microtubule-actin cross-linking factor 1 |
| 90 | KPRsPPRAL | 249 | 257 | A/C | Q86TG8 | Retrotransposon-derived protein PEG11 |

Figure 2

| | | | | | |
|---|---|---|---|---|---|
| 91 | KPRsPPPRALVL | 249 | | A | Q86TG8 | Retrotransposon-derived protein PEG11 |
| 92 | KPRsPVVEL | 667 | 259 | A/B/C | P25098 | Beta-Adrenergic receptor kinase 1 |
| 93 | KPSsPRGSLL | 134 | 675 | A | Q96IF1 | Protein ajuba |
| 94 | KRPEsPPSI | 254 | 143 | A | Q6P2C6 | AF-17 protein/ MLLT6 protein |
| 95 | LPAsPRARL | 443 | 262 | A/B | Q3KQU3 | Map 7 domain-containing protein 1 |
| 96 | LPIFSRLsI | 483 | 451 | A/B | P47974 | Zinc finger protein 36, C3H1 type-like 2 |
| 97 | LPKsPPYTAF | 90 | 491 | A | P23588 | Eukaryotic translation initiation factor 4B |
| 98 | LPRGSsPSVL | 105 | 99 | A/B | Q9GZN2 | Homeobox protein, TGFB induced factor 2/TGF2 |
| 99 | LPRMIsHSEL | 22 | 114 | A | O15172 | Putative phosphoserine phosphatase-like |
| 100 | PARsPVTEI | 187 | 31 | B | Q86YC2 | Partner and localizer of BRCA2, PALB2 |
| 101 | QPSFPsVLPA | | 195 | A | | No data base hit |
| 102 | RAHsSPASL | 124 | | B | P46937 | Yorkie homolog |
| 103 | RAPsPSSSRM | 2423 | 132 | A | Q9UQ35 | Serine/arginine repetitive matrix protein 2 |
| 104 | RARGIsPIVF | 303 | 2431 | B | Q96MU7 | YTH domain containing protein 1 |
| 105 | RLLsPQQPAL | 177 | 312 | A | Q14814 | Myocyte-specific enhancer factor 2D |
| 106 | RPAKsMDSL | 323 | 186 | A | Q7Z6I6 | Rho GTPase-activating protein 30 |
| 107 | RPAsAGAML | 198 | 331 | B | Q14814 | Monocyte-specific enhancer factor 2D |
| 108 | RPAsARAQPGL | 57 | 206 | A | Q9NPB0 | Uncharacterized protein C6orf64 |
| 109 | RPAsPAAKL | 512 | 67 | A/B | Q9P2N6 | KIAA1310 |
| 110 | RPAsPGPSL | 646 | 520 | A/B | Q8IY33 | MICAL-like protein 2 |
| 111 | RPAsPQRAQL | | 654 | A/B | | No data base hit |
| 112 | RPAsPSLQL | 277 | 285 | A/B | Q8WUF5 | RelA-associated inhibitor |
| 113 | RPAsPSLQLL | 277 | 286 | A/B | Q8IY33 | MICAL-like protein 2 |
| 114 | RPAsRFEVL | 384 | 392 | B | Q8IZ52 | Chondroitin sulfate synthase 2 |
| 115 | RPDsPTRPTL | 1646 | 1655 | A | Q7RTP6 | Protein MICAL-3 |

Figure 2 (cont.)

| # | Sequence | | | | ID | Description |
|---|---|---|---|---|---|---|
| 116 | RPDsRLGKTEL | 1225 | 1235 | A | Q9BYW2 | Histone-lysine N-methyltransferase, SETD2 |
| 117 | RPFARsHSF/RPFARSHsF | 1534 | 1542 | A | Q9BX84 | Transient receptor potential cation channel, sub M, mem 6 TRPM6 |
| 118 | RPFHGISTVsL | 1417 | 1427 | B | Q5VZ89 | DENN domain containing protein 4C |
| 119 | RPFsPREAL | 742 | 750 | A/B/C | Q86V48 | Leucine zipper protein 1 |
| 120 | RPHtPTGIYM | 198 | 208 | B | P62995 | Transformer-2 protein homolg beta |
| 121 | RPIsPGLSY | 364 | 372 | B/C | Q16204 | Coiled-coil domain containing protein 6 |
| 122 | RPNsPSPTAL | 185 | 194 | A/B | Q9UKI8 | Serine/threonine-protein kinase tousled-like 1 |
| 123 | RPPsPGPVL | 934 | 942 | A/B | Q12770 | SREPB cleavage-activating protein |
| 124 | RPPsSEFLDL | 476 | 485 | A/B | Q9P2R6 | Arginine-glutamic acid dipeptide repeats protein |
| 125 | RPQRAtSNVF | 13 | 22 | A/B | P19105 | Myosin regulatory light chain 12A |
| 126 | RPRARsVDAL | 488 | 497 | A/B/C | Q86X29 | Lipolysis-stimulated lipoprotein receptor |
| 127 | RPRLSsTNSSRF | | | A | | No data base hit |
| 128 | RPRPVsPSSL | 430 | 439 | A/B | P57059 | Serine/threonine-protein kinase SIK1 |
| 129 | RPRSLsSPTV | 443 | 452 | A | Q96PU5 | E3 ubiquitin-protein ligase NEDD4-like |
| 130 | RPRSLsSPTVTL | 443 | 454 | A | Q96PU5 | E3 ubiquitin-protein ligase NEDD4-like |
| 131 | RPRsPGSNSKV | 671 | 681 | A/B/C | P78347 | General transcription factor III |
| 132 | RPRsPNMQDL | 214 | 223 | B | Q6T310 | Ras-like protein family member 11A |
| 133 | RPRsPRENSI | 689 | 698 | A/B | Q99700 | Ataxin-2 |
| 134 | RPRsPRQNSI | 689 | 698 | A/B/C | Q99700 | Ataxin-2 with point mutation |
| 135 | RPRSTsQSIVSL | 841 | 852 | A | Q70EL4 | Ubiquitin carboxyl-terminal hydrolase 43 |
| 136 | RPSsLPDL | 661 | 668 | A | Q8NFD5 | AT-rich interactive domain-containing protein 1B |
| 137 | RPsSPALYF | 261 | 269 | A | Q9Y3Q8 | TSC22 domain family protein 4 |
| 138 | RPTsRLNRL | 860 | 868 | A/B/C | Q15788 | Nuclear receptor coactivator 1 |
| 139 | RPVsPFQEL | | | A/B/C | | No database hit |
| 140 | RPVsPGKDI | 406 | 414 | | P31629 | Transcription factor HIVEP2 |

Figure 2 (cont.)

| | | | | | |
|---|---|---|---|---|---|
| 141 | RPVtPVSDL | 63 | 71 | A | Q13118 | KLF10/ Krueppel-like factor 10 |
| 142 | RPWsPAVSA | 380 | 388 | A | P12755 | Ski oncogene |
| 143 | RPYsPSQYAL/RPYSPsQAL | 575 | 584 | A | F5H1B7 | Nuclear factor erythroid 2-related factor-1, NFE2L1 |
| 144 | RSRsPRPAL | | | A | | No data base hit |
| 145 | RTRsPSPTL | 515 | 523 | B | Q86UU1 | Pleckstrin homology-like domain family B |
| 146 | SKRGyIGL | | | A | | No data base hit |
| 147 | SPAsPKISL | 493 | 501 | A/B | Q8WWM7 | Ataxin-2-like protein |
| 148 | SPFKRQLsL | 317 | 325 | A/B/C | Q9Y6R0 | Numb homolog (Drosophila )- like |
| 149 | SPGsPRPAL | 391 | 399 | A | Q9H2I1 | DNA replication factor Cdt1 |
| 150 | SPKsPTAAL | 425 | 433 | A/B | Q53EZ4 | Centrosomal protein of 55 kDa, mitotic exit and cytokinesis |
| 151 | SPLTKSIsL | 1683 | 1691 | A/B | Q12802 | A-kinase anchor protein 13 |
| 152 | SPRERsPAL | 243 | 251 | A | Q9Y2W1 | Thyroid hormone receptor associated protein 3 |
| 153 | SPRPPNsPSI | 222 | 231 | A | Q8IZW8 | Tensin-4 |
| 154 | SPRRsLGLAL | 1382 | 1391 | A | Q8NEY1 | Neuron navigator 1 |
| 155 | SPRRsRSISL | 159 | 168 | A/B/C | Q16629 | Serine/Arginine-rich splicing factor 7 |
| 156 | SPRsITSTP | 290 | 298 | A | Q9P0K7 | Ankycorbin |
| 157 | SPRsPGKPM | | | A/C | | No data base hit |
| 158 | SPRsPGRSL | | | A/B/C | | No data base hit |
| 159 | SPRsPSTTYL | 772 | 781 | A/C | Q13111 | Chromatin assembly factor 1 subunit A |
| 160 | SPVsPMKEL | 22 | 30 | B | Q3KP66 | Uncharacterized protein C1orf106 |
| 161 | SPVsTRPLEP/SPVStRPLEP | 1534 | 1542 | A | Q9BX84 | Transient receptor potential cation channel, sub M, mem 6 TRPM6 |
| 162 | SRSsSVLsL | 636 | 644 | A | A1L390 | PLEKHG3/ Pleckstrin homology domain-containing family G member 3 |
| 163 | SVRsLSLSL | 280 | 288 | A | Q9Y446 | Plakophilin3 |
| 164 | TPRsPPLGL | 755 | 763 | A/B/C | Q16584 | Mitogen-activated protein kinase kinase kinase 11 |
| 165 | TPRsPPLGLI | 755 | 764 | A/B/C | Q16584 | Mitogen-activated protein kinase kinase kinase 11 |

Figure 2 (cont.)

| 166 | TQSSGKsSV | 33 | | A | Q00429 | Dynamin-1-like protein |
|---|---|---|---|---|---|---|
| 167 | VPKsPAFAL | 483 | 491 | B | Q9ULW0 | Targeting protein for Xklp2 |
| 168 | VPTsPKSSL | 1151 | 1159 | A | Q70E73 | Ras-associated and pleckstrin homology domains-containing protein 1 |
| 169 | VPVsPGQQL | 1277 | 1285 | A | Q9H4Z2 | Zinc finger protein 335, NRC-interacting factor1 |
| 170 | YPSFRRsSL | 280 | 288 | A/B | O95071 | E3 ubiquitin-protein ligase UBR5 |
| 171 | YPSsPRKAL | 159 | 167 | A | O43166 | Signal induced proliferation associated 1-like 1 |

Column 2: Phosphopeptide sequences; pSer, pThr and pTyr are specified by s, t, and y, respectively.
Column 3 & 4: Entries define the location of the phosphopeptides within the sequence of the parent protein.
Column 5: Protein identifier in the UniProt database, http://www.uniprot.org
Column 6: Name of the protein in the UniProt database.

Figure 2 (cont.)

SEQUENCE LISTING

```
<160> NUMBER OF SEQ ID NOS: 175

<210> SEQ ID NO 1
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 1

Arg Leu Asp Ser Tyr Val Arg Ser Leu
1               5

<210> SEQ ID NO 2
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 2

Arg Gln Asp Ser Thr Pro Gly Lys Val Phe Leu
1               5                   10

<210> SEQ ID NO 3
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 3

Val Leu Lys Gly Ser Arg Ser Ser Glu Leu
1               5                   10

<210> SEQ ID NO 4
<211> LENGTH: 9
<212> TYPE: PRT
<213> ORGANISM: Homo sapiens
```

```
<220> FEATURE:
<221> NAME/KEY: MOD_RES
<222> LOCATION: (3)..(3)
<223> OTHER INFORMATION: Phosphorylated residue

<400> SEQUENCE: 4

Arg Leu Ser Ser Pro Leu His Phe Val
1               5

<210> SEQ ID NO 5
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 5

Arg Leu Gln Ser Thr Ser Glu Arg Leu
1               5

<210> SEQ ID NO 6
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 6

Ala Met Ala Ala Ser Pro His Ala Val
1               5

<210> SEQ ID NO 7
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 7

Lys Leu Ala Ser Pro Glu Leu Glu Arg Leu
1               5                   10

<210> SEQ ID NO 8
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 8

Ile Leu Lys Ser Pro Glu Ile Gln Arg Ala
1               5                   10

<210> SEQ ID NO 9
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
```

```
<400> SEQUENCE: 9

Lys Leu Leu Ser Pro Ser Asn Glu Lys Leu
1               5                   10

<210> SEQ ID NO 10
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated residue

<400> SEQUENCE: 10

Lys Leu Leu Asp Phe Gly Ser Leu Ser Asn Leu Gln Val
1               5                   10

<210> SEQ ID NO 11
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated residue

<400> SEQUENCE: 11

Lys Leu Leu Ser Ser Ala Gln Arg Thr Leu
1               5                   10

<210> SEQ ID NO 12
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 12

Tyr Leu Asp Ser Gly Ile His Ser Gly Ala
1               5                   10

<210> SEQ ID NO 13
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 13

Gly Leu Leu Gly Ser Pro Val Arg Ala
1               5

<210> SEQ ID NO 14
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 14

Arg Val Ala Ser Pro Thr Ser Gly Val
```

```
1               5

<210> SEQ ID NO 15
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 15

Ile Met Asp Arg Thr Pro Glu Lys Leu
1               5

<210> SEQ ID NO 16
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 16

Val Met Ile Gly Ser Pro Lys Lys Val
1               5

<210> SEQ ID NO 17
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 17

Arg Thr Leu Ser His Ile Ser Glu Ala
1               5

<210> SEQ ID NO 18
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 18

Lys Met Asp Ser Phe Leu Asp Met Gln Leu
1               5                   10

<210> SEQ ID NO 19
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
<220> FEATURE:
<221> NAME/KEY: MOD_RES
<222> LOCATION: (8)..(8)
<223> OTHER INFORMATION: Leu or Ile

<400> SEQUENCE: 19

Leu Met Phe Ser Val Thr Ser Xaa
```

```
1               5

<210> SEQ ID NO 20
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 20

Ser Leu Gln Pro Arg Ser His Ser Val
1               5

<210> SEQ ID NO 21
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 21

Arg Leu Leu Ser Pro Leu Ser Ser Ala
1               5

<210> SEQ ID NO 22
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated residue

<400> SEQUENCE: 22

Ser Met Thr Arg Ser Pro Pro Arg Val
1               5

<210> SEQ ID NO 23
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 23

Arg Gln Ile Ser Gln Asp Val Lys Leu
1               5

<210> SEQ ID NO 24
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 24

Arg Gln Ala Ser Ile Glu Leu Pro Ser Met
1               5                   10

<210> SEQ ID NO 25
```

```
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 25

Arg Gln Ala Ser Ile Glu Leu Pro Ser Met Ala Val
1               5                   10

<210> SEQ ID NO 26
<211> LENGTH: 8
<212> TYPE: PRT
<213> ORGANISM: Homo sapiens

<400> SEQUENCE: 26

Ser Leu Leu Thr Phe Trp Asn Leu
1               5

<210> SEQ ID NO 27
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 27

Lys Val Gln Val Thr Ser Leu Ser Val
1               5

<210> SEQ ID NO 28
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 28

Val Leu Leu Ser Pro Val Pro Glu Leu
1               5

<210> SEQ ID NO 29
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 29

Arg Leu Gln Ser Thr Ser Glu Arg Leu
1               5

<210> SEQ ID NO 30
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
```

```
<400> SEQUENCE: 30

Thr Leu Ala Ser Pro Ser Val Phe Lys Ser Thr
1               5                   10

<210> SEQ ID NO 31
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 31

Arg Thr Tyr Ser Gly Pro Met Asn Lys Val
1               5                   10

<210> SEQ ID NO 32
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated residue

<400> SEQUENCE: 32

Lys Leu Ile Asp Ile Val Ser Ser Gln Lys Val
1               5                   10

<210> SEQ ID NO 33
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 33

Arg Thr Phe Ser Pro Thr Tyr Gly Leu
1               5

<210> SEQ ID NO 34
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 34

Ala Leu Tyr Ser Pro Ala Gln Pro Ser Leu
1               5                   10

<210> SEQ ID NO 35
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 35

Arg Gln Ile Ser Gln Asp Val Lys Leu
1               5
```

<210> SEQ ID NO 36
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 36

Ala Val Val Ser Pro Pro Ala Leu His Asn Ala
 1               5                  10

<210> SEQ ID NO 37
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 37

Arg Leu Asp Ser Tyr Val Arg Ser
 1               5

<210> SEQ ID NO 38
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated residue

<400> SEQUENCE: 38

His Pro Lys Arg Ser Val Ser Leu
 1               5

<210> SEQ ID NO 39
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 39

Leu Pro Ala Ser Pro Arg Ala Arg Leu
 1               5

<210> SEQ ID NO 40
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 40

His Pro Arg Ser Pro Thr Pro Thr Leu
 1               5

<210> SEQ ID NO 41
<211> LENGTH: 9

```
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 41

Tyr Pro Ser Ser Pro Arg Lys Ala Leu
1               5

<210> SEQ ID NO 42
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 42

Lys Pro Arg Ser Pro Pro Arg Ala Leu
1               5

<210> SEQ ID NO 43
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 43

Arg Pro Ala Lys Ser Met Asp Ser Leu
1               5

<210> SEQ ID NO 44
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 44

Lys Pro Arg Ser Pro Val Val Glu Leu
1               5

<210> SEQ ID NO 45
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
<220> FEATURE:
<221> NAME/KEY: MOD_RES
<222> LOCATION: (9)..(9)
<223> OTHER INFORMATION: Leu or Ile

<400> SEQUENCE: 45

Arg Ser Arg Ser Pro Arg Pro Ala Xaa
1               5

<210> SEQ ID NO 46
<211> LENGTH: 10
```

<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 46

Ala Pro Arg Ser Pro Pro Ser Arg Pro
1               5

<210> SEQ ID NO 47
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 47

Arg Pro Ser Gly Arg Arg Glu Ser Leu
1               5

<210> SEQ ID NO 48
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 48

Arg Pro Arg Arg Ser Ser Thr Gln Leu
1               5

<210> SEQ ID NO 49
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 49

Arg Pro Arg Ser Pro Pro Pro Arg Ala Pro
1               5                   10

<210> SEQ ID NO 50
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 50

Arg Pro Arg Ser Pro Gly Ser Asn Ser Lys Val
1               5                   10

<210> SEQ ID NO 51
<211> LENGTH: 9
<212> TYPE: PRT
<213> ORGANISM: Homo sapiens
<220> FEATURE:
<221> NAME/KEY: MOD_RES

```
<222> LOCATION: (8)..(8)
<223> OTHER INFORMATION: Phosphorylated residue

<400> SEQUENCE: 51

Gly Ala Gln Pro Gly Arg His Ser Val
1               5

<210> SEQ ID NO 52
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 52

Ser Pro Arg Ser Ile Thr Ser Thr Pro
1               5

<210> SEQ ID NO 53
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 53

Lys Ala Arg Ser Pro Gly Arg Ala Leu
1               5

<210> SEQ ID NO 54
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
<220> FEATURE:
<221> NAME/KEY: MOD_RES
<222> LOCATION: (9)..(9)
<223> OTHER INFORMATION: Leu or Ile

<400> SEQUENCE: 54

Ser Pro Arg Ser Pro Gly Arg Ser Xaa
1               5

<210> SEQ ID NO 55
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 55

Leu Pro Arg Gly Ser Ser Pro Ser Val Leu
1               5                   10

<210> SEQ ID NO 56
<211> LENGTH: 9
<212> TYPE: PRT
<213> ORGANISM: Homo sapiens
<220> FEATURE:
<221> NAME/KEY: MOD_RES
```

```
<222> LOCATION: (4)..(4)
<223> OTHER INFORMATION: Phosphorylated residue

<400> SEQUENCE: 56

Phe Pro His Ser Leu Leu Ser Val Ile
1               5

<210> SEQ ID NO 57
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 57

Ser Pro Arg Glu Arg Ser Pro Ala Leu
1               5

<210> SEQ ID NO 58
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 58

Ala Pro Arg Arg Tyr Ser Ser Ser Leu
1               5

<210> SEQ ID NO 59
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 59

Arg Thr Phe Ser Pro Thr Tyr Gly Leu
1               5

<210> SEQ ID NO 60
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 60

Ser Pro Phe Lys Arg Gln Leu Ser Leu
1               5

<210> SEQ ID NO 61
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 61
```

```
Ser Pro Arg Ser Pro Ser Thr Thr Tyr Leu
1               5                   10

<210> SEQ ID NO 62
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
<220> FEATURE:
<221> NAME/KEY: MOD_RES
<222> LOCATION: (6)..(6)
<223> OTHER INFORMATION: Lys or Gln
<220> FEATURE:
<221> NAME/KEY: MOD_RES
<222> LOCATION: (9)..(9)
<223> OTHER INFORMATION: Lys or Gln
<220> FEATURE:
<221> NAME/KEY: MOD_RES
<222> LOCATION: (10)..(10)
<223> OTHER INFORMATION: Leu or Ile

<400> SEQUENCE: 62

Arg Pro Ala Ser Pro Xaa Arg Ala Xaa Xaa
1               5                   10

<210> SEQ ID NO 63
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 63

Lys Leu Phe Pro Asp Thr Pro Leu Ala Leu
1               5                   10

<210> SEQ ID NO 64
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 64

Arg Leu Leu Ser Pro Leu Ser Ser Ala
1               5

<210> SEQ ID NO 65
<211> LENGTH: 7
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 65

Arg Leu Asp Ser Tyr Val Arg
1               5

<210> SEQ ID NO 66
<211> LENGTH: 10
```

```
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 66

Arg Gln Ala Ser Ile Glu Leu Pro Ser Met
1               5                   10

<210> SEQ ID NO 67
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 67

Lys Leu Met Ser Pro Lys Ala Asp Val Lys Leu
1               5                   10

<210> SEQ ID NO 68
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated residue

<400> SEQUENCE: 68

Ser Met Thr Arg Ser Pro Pro Arg Val
1               5

<210> SEQ ID NO 69
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 69

Arg Leu Phe Ser Lys Glu Leu Arg Cys
1               5

<210> SEQ ID NO 70
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 70

Ala Pro Arg Lys Gly Ser Phe Ser Ala Leu Met
1               5                   10

<210> SEQ ID NO 71
<211> LENGTH: 11
<212> TYPE: PRT
<213> ORGANISM: Homo sapiens
<220> FEATURE:
<221> NAME/KEY: MOD_RES
```

```
<222> LOCATION: (4)..(4)
<223> OTHER INFORMATION: Phosphorylated residue

<400> SEQUENCE: 71

Ala Leu Asp Ser Gly Ala Ser Leu Leu His Leu
1               5                   10

<210> SEQ ID NO 72
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 72

Ala Pro Leu Ala Arg Ala Ser Ser Leu
1               5

<210> SEQ ID NO 73
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 73

Ala Pro Arg Ala Pro Ser Ala Ser Pro Leu Ala Leu
1               5                   10

<210> SEQ ID NO 74
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 74

Ala Pro Arg Lys Gly Ser Phe Ser Ala Leu
1               5                   10

<210> SEQ ID NO 75
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 75

Ala Pro Ser Val Arg Ser Leu Ser Leu
1               5

<210> SEQ ID NO 76
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 76
```

```
Ala Pro Ser Val Arg Ser Leu Ser Leu
1               5
```

<210> SEQ ID NO 77
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 77

```
Phe Pro His Ser Leu Leu Ser Val Ile
1               5
```

<210> SEQ ID NO 78
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 78

```
Gly Pro Arg Pro Gly Ser Pro Ser Ala Leu
1               5                   10
```

<210> SEQ ID NO 79
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 79

```
Gly Pro Arg Ser Pro Pro Val Thr Leu
1               5
```

<210> SEQ ID NO 80
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated residue

<400> SEQUENCE: 80

```
Gly Arg Thr Gly Leu Pro Asp Leu
1               5
```

<210> SEQ ID NO 81
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated residue

<400> SEQUENCE: 81

```
His Pro Lys Arg Ser Val Ser Leu
1               5
```

```
<210> SEQ ID NO 82
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 82

His Pro Arg Ser Pro Asn Val Leu Ser Val
1               5                   10

<210> SEQ ID NO 83
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 83

His Pro Arg Ser Pro Thr Pro Thr Leu
1               5

<210> SEQ ID NO 84
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 84

Lys Ala Phe Ser Pro Val Arg Ser Val
1               5

<210> SEQ ID NO 85
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 85

Lys Ala Arg Ser Pro Gly Arg Ala Leu
1               5

<210> SEQ ID NO 86
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
<220> FEATURE:
<221> NAME/KEY: MOD_RES
<222> LOCATION: (8)..(8)
<223> OTHER INFORMATION: Phosphorylated residue

<400> SEQUENCE: 86

Lys Pro Glu Ser Arg Arg Ser Ser Leu Leu
1               5                   10
```

```
<210> SEQ ID NO 87
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 87

Lys Pro Leu Ile Arg Ser Gln Ser Leu
1               5

<210> SEQ ID NO 88
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 88

Lys Pro Arg Pro Pro Pro Leu Ser Pro
1               5

<210> SEQ ID NO 89
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 89

Lys Pro Arg Ser Pro Asp His Val Leu
1               5

<210> SEQ ID NO 90
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 90

Lys Pro Arg Ser Pro Pro Arg Ala Leu
1               5

<210> SEQ ID NO 91
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 91

Lys Pro Arg Ser Pro Pro Arg Ala Leu Val Leu
1               5                   10

<210> SEQ ID NO 92
<211> LENGTH: 9
<212> TYPE: PRT
```

```
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 92

Lys Pro Arg Ser Pro Val Val Glu Leu
1               5

<210> SEQ ID NO 93
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 93

Lys Pro Ser Ser Pro Arg Gly Ser Leu Leu
1               5                   10

<210> SEQ ID NO 94
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 94

Lys Arg Pro Glu Ser Pro Pro Ser Ile
1               5

<210> SEQ ID NO 95
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 95

Leu Pro Ala Ser Pro Arg Ala Arg Leu
1               5

<210> SEQ ID NO 96
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 96

Leu Pro Ile Phe Ser Arg Leu Ser Ile
1               5

<210> SEQ ID NO 97
<211> LENGTH: 10
<212> TYPE: PRT
<213> ORGANISM: Homo sapiens
<220> FEATURE:
<221> NAME/KEY: MOD_RES
<222> LOCATION: (4)..(4)
```

<223> OTHER INFORMATION: Phosphorylated residue

<400> SEQUENCE: 97

Leu Pro Lys Ser Pro Pro Tyr Thr Ala Phe
1               5                   10

<210> SEQ ID NO 98
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 98

Leu Pro Arg Gly Ser Ser Pro Ser Val Leu
1               5                   10

<210> SEQ ID NO 99
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 99

Leu Pro Arg Met Ile Ser His Ser Glu Leu
1               5                   10

<210> SEQ ID NO 100
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 100

Pro Ala Arg Ser Pro Val Thr Glu Ile
1               5

<210> SEQ ID NO 101
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 101

Gln Pro Ser Phe Pro Ser Val Leu Pro Ala
1               5                   10

<210> SEQ ID NO 102
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 102

Arg Ala His Ser Ser Pro Ala Ser Leu
1               5

<210> SEQ ID NO 103
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 103

Arg Ala Pro Ser Pro Ser Ser Arg Met
1               5

<210> SEQ ID NO 104
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 104

Arg Ala Arg Gly Ile Ser Pro Ile Val Phe
1               5                   10

<210> SEQ ID NO 105
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 105

Arg Leu Leu Ser Pro Gln Gln Pro Ala Leu
1               5                   10

<210> SEQ ID NO 106
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 106

Arg Pro Ala Lys Ser Met Asp Ser Leu
1               5

<210> SEQ ID NO 107
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 107

Arg Pro Ala Ser Ala Gly Ala Met Leu
1               5

```
<210> SEQ ID NO 108
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 108

Arg Pro Ala Ser Ala Arg Ala Gln Pro Gly Leu
1               5                   10

<210> SEQ ID NO 109
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 109

Arg Pro Ala Ser Pro Ala Ala Lys Leu
1               5

<210> SEQ ID NO 110
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 110

Arg Pro Ala Ser Pro Gly Pro Ser Leu
1               5

<210> SEQ ID NO 111
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 111

Arg Pro Ala Ser Pro Gln Arg Ala Gln Leu
1               5                   10

<210> SEQ ID NO 112
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 112

Arg Pro Ala Ser Pro Ser Leu Gln Leu
1               5

<210> SEQ ID NO 113
<211> LENGTH: 10
<212> TYPE: PRT
<213> ORGANISM: Homo sapiens
```

```
<220> FEATURE:
<221> NAME/KEY: MOD_RES
<222> LOCATION: (4)..(4)
<223> OTHER INFORMATION: Phosphorylated residue

<400> SEQUENCE: 113

Arg Pro Ala Ser Pro Ser Leu Gln Leu Leu
1               5                   10

<210> SEQ ID NO 114
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 114

Arg Pro Ala Ser Arg Phe Glu Val Leu
1               5

<210> SEQ ID NO 115
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 115

Arg Pro Asp Ser Pro Thr Arg Pro Thr Leu
1               5                   10

<210> SEQ ID NO 116
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 116

Arg Pro Asp Ser Arg Leu Gly Lys Thr Glu Leu
1               5                   10

<210> SEQ ID NO 117
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 117

Arg Pro Phe Ala Arg Ser His Ser Phe
1               5

<210> SEQ ID NO 118
<211> LENGTH: 11
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated residue
```

```
<400> SEQUENCE: 118

Arg Pro Phe His Gly Ile Ser Thr Val Ser Leu
1               5                   10

<210> SEQ ID NO 119
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 119

Arg Pro Phe Ser Pro Arg Glu Ala Leu
1               5

<210> SEQ ID NO 120
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 120

Arg Pro His Thr Pro Thr Gly Ile Tyr Met
1               5                   10

<210> SEQ ID NO 121
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 121

Arg Pro Ile Ser Pro Gly Leu Ser Tyr
1               5

<210> SEQ ID NO 122
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 122

Arg Pro Asn Ser Pro Ser Pro Thr Ala Leu
1               5                   10

<210> SEQ ID NO 123
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 123

Arg Pro Pro Ser Pro Gly Pro Val Leu
```

<210> SEQ ID NO 124
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 124

Arg Pro Pro Ser Ser Glu Phe Leu Asp Leu
1               5                   10

<210> SEQ ID NO 125
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 125

Arg Pro Gln Arg Ala Thr Ser Asn Val Phe
1               5                   10

<210> SEQ ID NO 126
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 126

Arg Pro Arg Ala Arg Ser Val Asp Ala Leu
1               5                   10

<210> SEQ ID NO 127
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 127

Arg Pro Arg Leu Ser Ser Thr Asn Ser Ser Arg Phe
1               5                   10

<210> SEQ ID NO 128
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 128

Arg Pro Arg Pro Val Ser Pro Ser Ser Leu
1               5                   10

<210> SEQ ID NO 129

```
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 129

Arg Pro Arg Ser Leu Ser Ser Pro Thr Val
1               5                   10

<210> SEQ ID NO 130
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 130

Arg Pro Arg Ser Leu Ser Ser Pro Thr Val Thr Leu
1               5                   10

<210> SEQ ID NO 131
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 131

Arg Pro Arg Ser Pro Gly Ser Asn Ser Lys Val
1               5                   10

<210> SEQ ID NO 132
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 132

Arg Pro Arg Ser Pro Asn Met Gln Asp Leu
1               5                   10

<210> SEQ ID NO 133
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 133

Arg Pro Arg Ser Pro Arg Glu Asn Ser Ile
1               5                   10

<210> SEQ ID NO 134
<211> LENGTH: 10
<212> TYPE: PRT
<213> ORGANISM: Homo sapiens
<220> FEATURE:
```

```
<221> NAME/KEY: MOD_RES
<222> LOCATION: (4)..(4)
<223> OTHER INFORMATION: Phosphorylated residue

<400> SEQUENCE: 134

Arg Pro Arg Ser Pro Arg Gln Asn Ser Ile
1               5                   10

<210> SEQ ID NO 135
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 135

Arg Pro Arg Ser Thr Ser Gln Ser Ile Val Ser Leu
1               5                   10

<210> SEQ ID NO 136
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 136

Arg Pro Ser Ser Leu Pro Asp Leu
1               5

<210> SEQ ID NO 137
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated residue

<400> SEQUENCE: 137

Arg Pro Ser Ser Pro Ala Leu Tyr Phe
1               5

<210> SEQ ID NO 138
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 138

Arg Pro Thr Ser Arg Leu Asn Arg Leu
1               5

<210> SEQ ID NO 139
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
```

```
<400> SEQUENCE: 139

Arg Pro Val Ser Pro Phe Gln Glu Leu
1               5

<210> SEQ ID NO 140
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 140

Arg Pro Val Ser Pro Gly Lys Asp Ile
1               5

<210> SEQ ID NO 141
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 141

Arg Pro Val Thr Pro Val Ser Asp Leu
1               5

<210> SEQ ID NO 142
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 142

Arg Pro Trp Ser Pro Ala Val Ser Ala
1               5

<210> SEQ ID NO 143
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 143

Arg Pro Tyr Ser Pro Ser Gln Tyr Ala Leu
1               5                   10

<210> SEQ ID NO 144
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 144

Arg Ser Arg Ser Pro Arg Pro Ala Leu
1               5
```

<210> SEQ ID NO 145
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 145

Arg Thr Arg Ser Pro Ser Pro Thr Leu
1               5

<210> SEQ ID NO 146
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 146

Ser Lys Arg Gly Tyr Ile Gly Leu
1               5

<210> SEQ ID NO 147
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 147

Ser Pro Ala Ser Pro Lys Ile Ser Leu
1               5

<210> SEQ ID NO 148
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 148

Ser Pro Phe Lys Arg Gln Leu Ser Leu
1               5

<210> SEQ ID NO 149
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 149

Ser Pro Gly Ser Pro Arg Pro Ala Leu
1               5

<210> SEQ ID NO 150
<211> LENGTH: 9

```
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 150

Ser Pro Lys Ser Pro Thr Ala Ala Leu
1               5

<210> SEQ ID NO 151
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 151

Ser Pro Leu Thr Lys Ser Ile Ser Leu
1               5

<210> SEQ ID NO 152
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 152

Ser Pro Arg Glu Arg Ser Pro Ala Leu
1               5

<210> SEQ ID NO 153
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated residue

<400> SEQUENCE: 153

Ser Pro Arg Pro Pro Asn Ser Pro Ser Ile
1               5                   10

<210> SEQ ID NO 154
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 154

Ser Pro Arg Arg Ser Leu Gly Leu Ala Leu
1               5                   10

<210> SEQ ID NO 155
<211> LENGTH: 10
<212> TYPE: PRT
<213> ORGANISM: Homo sapiens
<220> FEATURE:
<221> NAME/KEY: MOD_RES
```

```
<222> LOCATION: (5)..(5)
<223> OTHER INFORMATION: Phosphorylated residue

<400> SEQUENCE: 155

Ser Pro Arg Arg Ser Arg Ser Ile Ser Leu
1               5                   10

<210> SEQ ID NO 156
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 156

Ser Pro Arg Ser Ile Thr Ser Thr Pro
1               5

<210> SEQ ID NO 157
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 157

Ser Pro Arg Ser Pro Gly Lys Pro Met
1               5

<210> SEQ ID NO 158
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 158

Ser Pro Arg Ser Pro Gly Arg Ser Leu
1               5

<210> SEQ ID NO 159
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 159

Ser Pro Arg Ser Pro Ser Thr Thr Tyr Leu
1               5                   10

<210> SEQ ID NO 160
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 160
```

Ser Pro Val Ser Pro Met Lys Glu Leu
1               5

<210> SEQ ID NO 161
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 161

Ser Pro Val Ser Thr Arg Pro Leu Glu Pro
1               5                   10

<210> SEQ ID NO 162
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue
<220> FEATURE:
<221> NAME/KEY: MOD_RES
<222> LOCATION: (8)..(8)
<223> OTHER INFORMATION: Phosphorylated residue

<400> SEQUENCE: 162

Ser Arg Ser Ser Ser Val Leu Ser Leu
1               5

<210> SEQ ID NO 163
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 163

Ser Val Arg Ser Leu Ser Leu Ser Leu
1               5

<210> SEQ ID NO 164
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 164

Thr Pro Arg Ser Pro Pro Leu Gly Leu
1               5

<210> SEQ ID NO 165
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 165

```
Thr Pro Arg Ser Pro Pro Leu Gly Leu Ile
1               5                   10

<210> SEQ ID NO 166
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated residue

<400> SEQUENCE: 166

Thr Gln Ser Ser Gly Lys Ser Ser Val
1               5

<210> SEQ ID NO 167
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 167

Val Pro Lys Ser Pro Ala Phe Ala Leu
1               5

<210> SEQ ID NO 168
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 168

Val Pro Thr Ser Pro Lys Ser Ser Leu
1               5

<210> SEQ ID NO 169
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 169

Val Pro Val Ser Pro Gly Gln Gln Leu
1               5

<210> SEQ ID NO 170
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Phosphorylated residue

<400> SEQUENCE: 170

Tyr Pro Ser Phe Arg Arg Ser Ser Leu
1               5
```

```
<210> SEQ ID NO 171
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 171

Tyr Pro Ser Ser Pro Arg Lys Ala Leu
1               5

<210> SEQ ID NO 172
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphorylated residue

<400> SEQUENCE: 172

Asp Arg Val Tyr Ile His Pro Phe
1               5

<210> SEQ ID NO 173
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated residue

<400> SEQUENCE: 173

Arg Pro Phe Ala Arg Ser His Ser Phe
1               5

<210> SEQ ID NO 174
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated residue

<400> SEQUENCE: 174

Arg Pro Tyr Ser Pro Ser Gln Tyr Ala Leu
1               5                   10

<210> SEQ ID NO 175
<211> LENGTH: 10
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Phosphorylated residue

<400> SEQUENCE: 175

Ser Pro Val Ser Thr Arg Pro Leu Glu Pro
1               5                   10
```

IDENTIFICATION OF MHC CLASS I PHOSPHO-PEPTIDE ANTIGENS FROM BREAST CANCER UTILIZING SHLA TECHNOLOGY AND COMPLEMENTARY ENRICHMENT STRATEGIES

CROSS-REFERENCE TO RELATED APPLICATIONS

This application is a 35 U.S.C. § 371 filing of International Patent Application No. PCT/US2013/042908, filed May 28, 2013, which claims priority to U.S. Provisional Patent Application Ser. Nos. 61/652,028, filed May 25, 2012; and 61/667,697, filed Jul. 3, 2012, the disclosures of each of which are incorporated by reference herein in their entireties.

SEQUENCE LISTING

The instant application contains a Sequence Listing which has been submitted in ASCII format via EFS-Web and is hereby incorporated by reference in its entirety. Said ASCII copy, created on May 28, 2013, is named 0099_0003WO1_SL.txt and is 39140 bytes in size.

US GOVERNMENT RIGHTS

This invention was made with United States Government support under Grant No. R01 AI33993 awarded by the National Institutes of Health. The United States Government has certain rights in the invention.

BACKGROUND

The mammalian immune system has evolved a variety of mechanisms to protect the host from cancerous cells. An important component of this response is mediated by cells referred to as T cells. Cytotoxic T lymphocytes (CTL) are specialized T cells that primarily function by recognizing and killing cancerous cells or infected cells, but they can also function by secreting soluble molecules referred to as ytokines that can mediate a variety of effects on the immune system. T helper cells primarily function by recognizing antigen on specialized antigen presenting cells, and in turn secreting cytokines that activate B cells, T cells, and macrophages.

A variety of evidence suggests that immunotherapy designed to stimulate a tumor-specific CTL response would be effective in controlling cancer. For example, it has been shown that human CTL recognize sarcomas (Slovin et al., 1986, J Immunol 137, 3042-3048), renal cell carcinomas (Schendel et al., 1993, J Immunol 151, 42094220), colorectal carcinomas (Jacob et al., 1997, Int J Cancer 71, 325-332), ovarian carcinomas (Peoples et al., 1993, Surgery 114, 227-234), pancreatic carcinomas (Peiper et al., 1997, Eur J Immunol 27, 1115-1123), squamous tumors of the head and neck (Yasumura et al., 1993, Cancer Res 53, 1461-1468), and squamous carcinomas of the lung (Slingluff et al., 1994, Cancer Res 54, 2731-2737; Yoshino et al., 1994, Cancer Res 54, 3387-3390). The largest number of reports of human tumor-reactive CTLs, however, has concerned melanomas (Boon et al., 1994, Annu Rev Immunol 12, 337365). The ability of tumor-specific CTL to mediate tumor regression, in both human (Parmiani et al., 2002, J Natl Cancer Inst 94, 805-818; Weber, 2002, Cancer Invest 20, 208-221) and animal models, suggests that methods directed at increasing CTL activity would likely have a beneficial effect with respect to tumor treatment.

Melanoma, or skin cancer, is a disease that is diagnosed in approximately 54,200 persons per year. Conventional therapy for the disease includes surgery, radiation therapy, and chemotherapy. In spite of these approaches to treatment, approximately 7,600 individuals die in the United States every year due to melanoma. Overall, the 5-year survival rate for the disease is 88%. The survival rate drops, however, in more advanced stages of the disease with only about 50% of Stage III patients, and 20-30% of Stage IV patients surviving past five years. In patients where the melanoma has metastasized to distant sites, the 5-year survival dips to only 12%. Clearly, there is a population of melanoma patients that is in need of better treatment options. More recently, in an attempt to decrease the number of deaths attributed to melanoma, immunotherapy has been added to the arsenal of treatments used against the disease.

In order for CTL to kill or secrete cytokines in response to a cancer cell, the CTL must first recognize the cancer cell (Townsend and Bodmer, 1989). This process involves the interaction of the T cell receptor, located on the surface of the CTL, with what is generically referred to as an MHC-peptide complex which is located on the surface of the cancerous cell. MHC (major histocompatibility-complex)-encoded molecules have been subdivided into two types, and are referred to as class I and class II MHC-encoded molecules. In the human immune system, MHC molecules are referred to as human leukocyte antigens (HLA). Within the MHC complex, located on chromosome six, are three different loci that encode for class I MHC molecules. MHC molecules encoded at these loci are referred to as HLA-A, HLA-B, and HLA-C. The genes that can be encoded at each of these loci are extremely polymorphic, and thus, different individuals within the population express different class I MHC molecules on the surface of their cells. HLA-A1, HLA-A2, HLA-A3, HLA-B7, and HLA-B8 are examples of different class I MHC molecules that can be expressed from these loci.

The peptides which associate with the MHC molecules can either be derived from proteins made within the cell, in which case they typically associate with class I MHC molecules (Rock and Goldberg, 1999, Annu Rev Immunol 17, 739-779); or they can be derived from proteins which are acquired from outside of the cell, in which case they typically associate with class II MHC molecules (Watts, 1997, Annu Rev Immunol 15, 821-850). The peptides that evoke a cancer-specific CTL response most typically associate with class I MHC molecules. The peptides themselves are typically nine amino acids in length, but can vary from a minimum length of eight amino acids to a maximum of twelve amino acids in length. Tumor antigens may also bind to class II MHC molecules on antigen presenting cells and provoke a T helper cell response. The peptides that bind to class II MHC molecules are generally twelve to nineteen amino acids in length, but can be as short as ten amino acids and as long as thirty amino acids.

The process by which intact proteins are degraded into peptides is referred to as antigen processing. Two major pathways of antigen processing occur within cells (Rock and Goldberg, 1999, Annu Rev Immunol 17, 739-779). One pathway, which is largely restricted to cells that are antigen presenting cells such as dendritic cells, macrophages, and B cells, degrades proteins that are typically phagocytosed or endocytosed into the cell. Peptides derived in this pathway typically bind to class II MHC molecules. A second pathway of antigen processing is present in essentially all cells of the body. This second pathway primarily degrades proteins that are made within the cells, and the peptides derived from this pathway primarily bind to class I MHC molecules. Antigen processing by this latter pathway involves polypeptide synthesis and proteolysis in the cytoplasm, followed by transport of peptides to the plasma membrane for presentation. These peptides, initially being transported into the endoplasmic reticulum of the cell, become associated with newly synthesized class I MHC molecules and the resulting complexes are then transported to the cell surface. Peptides derived from membrane and secreted proteins have also been identified. In some cases these peptides correspond to the signal sequence of the proteins which is cleaved from the protein by the signal peptidase. In other cases, it is thought that some fraction of the membrane and secreted proteins are transported from the endoplasmic reticulum into the cytoplasm where processing subsequently occurs.

Once bound to the class I MHC molecule, the peptides are recognized by antigen-specific receptors on CTL. Several methods have been developed to identify the peptides recognized by CTL, each method of which relies on the ability of a CTL to recognize and kill only those cells expressing the appropriate class I MHC molecule with the peptide bound to it. Mere expression of the class I MHC molecule is insufficient to trigger the CTL to kill the target cell if the antigenic peptide is not bound to the class I MHC molecule. Such peptides can be derived from a non-self source, such as a pathogen (for example, following the infection of a cell by a bacterium or a virus) or from a self-derived protein within a cell, such as a cancerous cell. The tumor antigens from which the peptides are derived can broadly be categorized as differentiation antigens, cancer/testis antigens, mutated gene products, widely expressed proteins, and viral antigens (Castelli et al., 2000, J Cell Physiol 182, 323-331).

Immunization with melanoma-derived, class I or class II MHC-encoded molecule associated peptides, or with a precursor polypeptide or protein that contains the peptide, or with a gene that encodes a polypeptide or protein containing the peptide, are forms of immunotherapy that can be employed in the treatment of melanoma. This form of immunotherapy requires that immunogens be identified so that they can be formulated into an appropriate vaccine. Although a large number of tumor-associated peptide antigens recognized by tumor reactive CTL have been identified, there are few examples of antigens that are derived from proteins that are selectively expressed on a broad array of tumors, as well as associated with cellular proliferation and/or transformation. Attractive candidates for this type of antigen are peptides derived from proteins that are differentially phosphorylated on serine (Ser), threonine (Thr), and tyrosine (Tyr) (Zarling et al., 2000, J Exp Med 192 1755-1762). Due to the increased phosphorylation of cellular proteins in transformed cells as compared to normal cells, there are likely to be new phosphorylated peptides presented on the cell surface available for recognition by CTL. However, these are not predictable from simple inspection of protein sequences, and the exact phosphorylation sites of many proteins, as well as their phosphorylation state in a tumor cell, remain unknown.

There is a long felt need in the art for methods of identifying tumor antigens, and for methods of treating or preventing cancer based on the use of such tumor antigens. The present invention satisfies these needs.

SUMMARY OF THE INVENTION

The present invention describes novel tumor-specific peptides and antibodies generated against said peptides. The peptides and antibodies described herein may be used as diagnostic indicators of the presence of cancer and/or used in therapeutics to treat and prevent cancer. For the present invention, mass spectrometry has been used to identify phosphorylated peptides associated with the class I MHC molecule HLA-A*0201 and HLA-B7 and displayed on melanoma cells. The invention also provides novel methods for identifying such peptides.

In one aspect, the cancer is breast cancer.

Various aspects and embodiments of the invention are described in further detail below.

BRIEF DESCRIPTION OF THE DRAWINGS

FIG. 1, comprising In FIG. 1A, two phosphopeptide-specific CTL cell lines, 6850 and 6960 that are specific for the phosphopeptide GLLGpSPVRA, recognize the phosphopeptide on all the cancer cell lines, but not the control cell line. In FIG. 1B, two phosphopeptide-specific CTL cell lines, 5183 and 63 that are specific for the phosphopeptide RVApSPTSGV, recognize the phosphopeptide on all the cancer cell lines, but not the control cell line. The ordinate indicates murine IFNγ in pg/ml. The abscissa indicates each cell line.

FIG. 2 presents a Table of phosphopeptides identified for breast cancer by the Class I MHC Molecule on the HLA B*0702 allele.

DETAILED DESCRIPTION OF THE INVENTION

Definitions

Figure 1A:
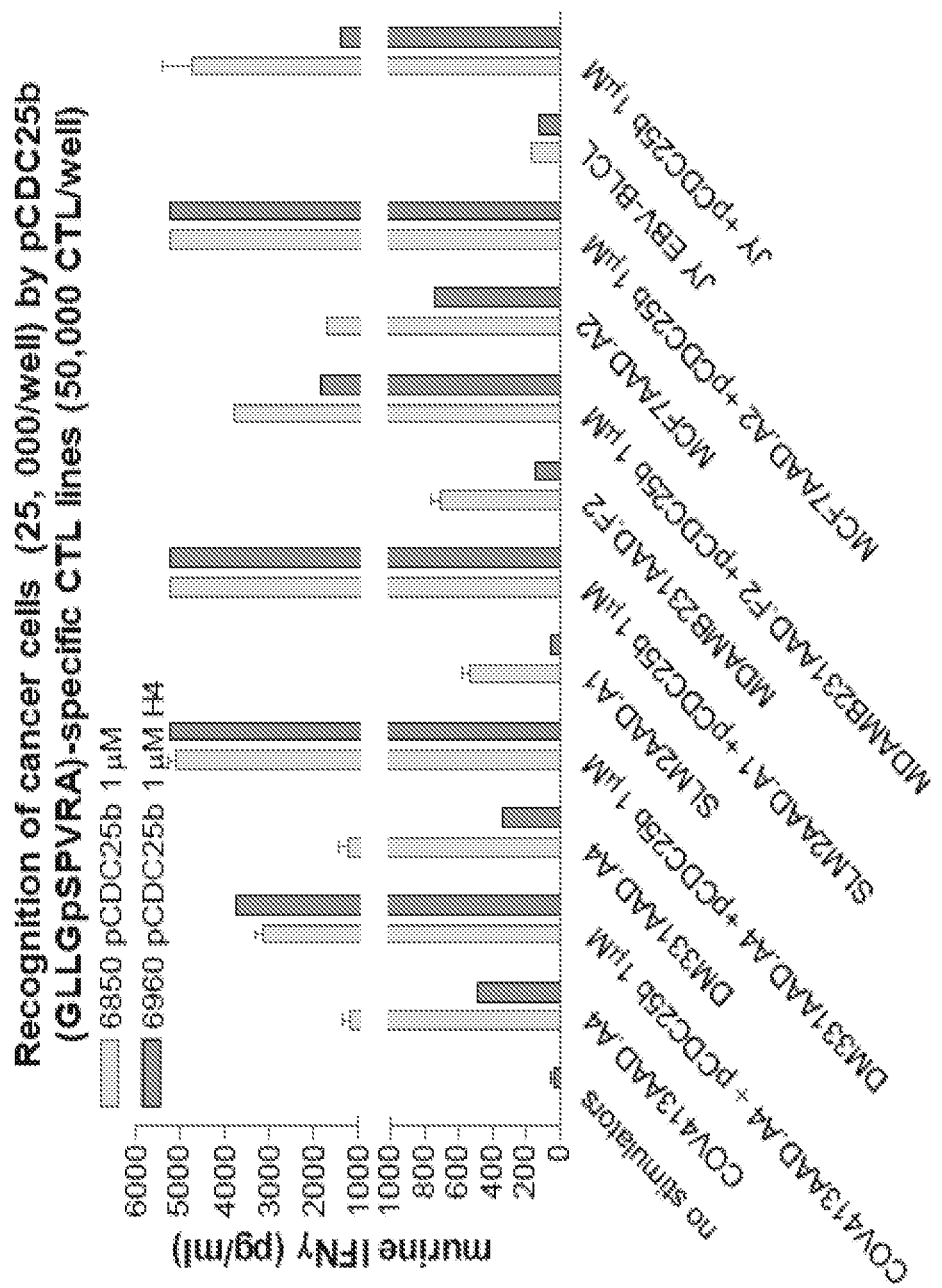
FIGS. 1A and 1B, is a graphic illustration of the recognition of naturally processed and presented phosphorylated peptides on cancer cells by the phosphopeptide-specific CTL. Phosphopeptide-specific CTL were incubated with the following cancer cell lines or EBV-transformed B lymphoblastoid cell lines (BLCL): COV413.AAD.A4 ovarian carcinoma, DM331.AAD.A4 and SLM2.AAD.A1 melanomas, MCF7.AAD.A2 and MDAMB231.AAD breast carcinomas, and JY EBV-BLCL. Supernatants were harvested and evaluated for the presence of murine IFNγ (produced by murine CTL lines). As a positive control, cancer cells were pulsed with the specific phosphopeptide to show that they are capable of presenting exogenously added peptide.

In describing and claiming the invention, the following terminology will be used in accordance with the definitions set forth below.

As used herein, the articles "a" and "an" refer to one or to more than one, i.e., to at least one, of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

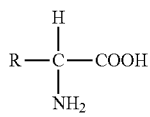

Amino acids may be classified into seven groups on the basis of the side chain (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

A disease or disorder is "alleviated" if the severity of a symptom of the disease or disorder, the frequency with which such a symptom is experienced by a patient, or both, are reduced. The term "antigen" as used herein is defined as a molecule that provokes an immune response. This immune response may involve either antibody production, or the activation of specific immunologically-competent cells, or both.

As used herein, the term "antibody" refers to a polyclonal or monoclonal antibody or a binding fragment thereof such as Fab, F(ab')2 and Fv fragments.

As used herein, the term "antigen peptide" refers to a phosphorylated amino acid sequence derived from a cancer cell, such as the sequences selected from the group consisting of SEQ ID NOs:70-171 or a peptide at least or about 80, 85, 90, 95, 98, 99, or 100% identical thereto.

As used herein, the term "cancer cell-specific phosphopeptide" refers to a phosphopeptide, which is expressed at higher levels in said cancer cell compared to its normal counterpart cell or tissue.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control ay be recorded so that the recorded results may be compared with results obtained by examination of a test cell, tissue, sample, or subject.

A "test" cell, tissue, sample, or subject is one being examined.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

As used herein, a "functional" biological molecule is a biological molecule in a form in which it exhibits a property or activity by which it is characterized. A functional enzyme, for example, is one which exhibits the characteristic catalytic activity by which the enzyme is characterized. "Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the)(BLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g.,)(BLAST and NBLAST) can be used. See http://www.ncbi.nlm.nih.gov.

The percent identity between two sequences can be determined using techniques similar to those described above, with or without allowing gaps. In calculating percent identity, typically exact matches are counted.

By the term "immunizing a subject against an antigen" is meant administering to a subject a composition, a peptide, a polypeptide, or a fragment, derivative, or modification thereof, a protein complex, a DNA encoding a protein complex, an antibody or a DNA encoding an antibody, which elicits an immune response in the human which immune response provides protection to the human against a disease caused by the antigen or an organism which expresses the antigen.

As used herein, an "instructional material" includes a publication, a recording, a diagram, or any other medium of expression, which can be used to communicate the usefulness of the composition of the invention for its designated use. The instructional material of the kit of the invention may, for example, be affixed to a container, which contains the composition or be shipped together with a container which contains the composition. Alternatively, the instructional material may be shipped separately from the container with the intention that the instructional material and the composition be used cooperatively by the recipient.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, a "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH$_2$OC(O)NR—), a phosphonate linkage, a —CH2-sulfonamide (—CH2-S(O)2NR—) linkage, a urea (—NHC(O)NH—) linkage, a —CH2-secondary amine linkage, or with an alkylated peptidyl linkage (—C(O)NR—) wherein R is C1-C4 alkyl;
2. peptides wherein the N-terminus is derivatized to a —NRR$_1$ group, to a —NRC(O)R group, to a —NRC(O)OR group, to a —NRS(O)2R group, to a —NHC(O)NHR group where R and R$_1$ are hydrogen or C1-C4 alkyl with the proviso that R and R1 are not both hydrogen;
3. peptides wherein the C terminus is derivatized to —C(O)R2 where R2 is selected from the group consisting of C1-C4 alkoxy, and —NR3R4 where R3 and R4 are independently selected from the group consisting of hydrogen and C1-C4 alkyl.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and Xaa or X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contains amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" is defined herein as an amino acid exchange within one of the following five groups:
I. Small aliphatic, nonpolar or slightly polar residues: Ala, Ser, Thr, Pro, Gly;
II. Polar, negatively charged residues and their amides: Asp, Asn, Glu, Gln;
III. Polar, positively charged residues: His, Arg, Lys;
IV. Large, aliphatic, nonpolar residues: Met Leu, Ile, Val, Cys
V. Large, aromatic residues: Phe, Tyr, Trp As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "subject" of diagnosis or treatment is a mammal, including a human.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

By the term "vaccine," as used herein, is meant a composition, which when inoculated into a mammal has the effect of stimulating a cellular immune response comprising a T cell response or a humoral immune response comprising a B cell response generally resulting in antibody production. The T cell response may be a cytotoxic T cell response directed against macromolecules produced by the bacteria. However, the induction of a T cell response comprising other types of T cells by the vaccine of the invention is also contemplated. A B cell response results in the production of antibody which binds to the antigen. The "vaccine" has the effect of stimulating an immune response in the subject, which serves to fully or partially protect the subject against a disease or its symptoms. The term vaccine encompasses prophylactic as well as therapeutic vaccines. A combination vaccine is one which combines two or more vaccines.

Embodiments of the Invention

The present invention is directed to novel phosphorylated peptides that give rise to cancer antigens. In one embodiment, for example, the phosphopeptides are those described in the tables of the invention, including Table 1, associated with Examples 1 and 2. Example 3 and Appendix have different Tables with other peptides, and all 5 sequences cited below are for Table 1 of Examples 1 and 2, but the embodiments cited are also useful for the results and sequences of Example 3 and Appendix A. In one aspect, the peptides bind to MHC molecules. In another aspect, the peptides of the invention stimulate an immune response. In yet another aspect, the peptides of the invention are recognized by a cell or molecule which is a product of, or is stimulated as 10 a result of, an immune response.

TABLE 1

Cancer Antigen Phosphopeptides

| Protein | Gi number | Sequence | HLA type | SEQ ID |
|---|---|---|---|---|
| MUM-2 | 20177848 | RLDpSYVRSL | HLA-A2.1 | 1 |
| Orphan nuclear receptor T2 | 36117 | RQDpSTPGKVFL | HLA-A2.1 | 2 |
| Riken ORF 32, chromosome 10 | 58864795 | VLKGpSRSSEL | HLA-A2.1 | 3 |
| ORF 17, chromosome 2 | 40787650 | RLpSSFLHFV | HLA-A2.1 | 4 |
| ATP-dependent metalloprotease | 14248493 | RLQpSTSERL | HLA-A2.1 | 5 |
| Heterogeneous nuclear ribonucleoprotein:A0 | 13938287 | AMAApSPHAV | HLA-A2.1 | 6 |
| Jun-b/c/d | 49456463 | KLApSPELERL | HLA-A2.1 | 7 |
| Ribosomal protein L4 | 22002063 | ILKpSPEIQRA | HLA-A2.1 | 8 |
| Ub-carboxyl terminal hydrolase-10 (USP-10) | 2501458 | KLLpSPSNEKL | HLA-A2.1 | 9 |
| Ribosomal protein S17 | 51476007 | KLLDFGSLpSNLQV | HLA-A2.1 | 10 |

TABLE 1 -continued

Cancer Antigen Phosphopeptides

| Protein | Gi number | Sequence | HLA type | SEQ ID |
|---|---|---|---|---|
| Krueppel-like zinc finger protein | 903598 | KLLSSAQRpTL | HLA-A2.1 | 11 |
| B-Catenin | 20384898 | YLDpSGIHSGA | HLA-A2.1 | 12 |
| CDC25b:p63 | 14602917 | GLLGpSPVRA | HLA-A2.1 | 13 |
| Insulin receptor substrate-2 | 55663292 | RVApSPTSGV | HLA-A2.1 | 14 |
| Breast cancer anti-estrogen resistance-3 (BCAR3) | 55663999 | IMDRpTPEKL | HLA-A2.1 | 15 |
| Tumor endothelial marker-6, thyroid specific PTB domain protein | 23451123 | VMIGpSPKKV | HLA-A2.1 | 16 |
| Hypothetical protein FAM65A protein | 32493393 | RTLpSHISEA | HLA-A2.1 | 17 |
| Nedd4 binding protein 2, BCL3 binding protein | 31742492 | KMDpSFLDMQL | HLA-A2.1 | 18 |
| Unknown (protein gi:22902182) | 22902182 | LMFpSVTS(L/I) | HLA-A2.1 | 19 |
| Pleckstrin homology domain-containing protein family A member 6 | 46397654 | SLQPRSHpSV | HLA-A2.1 | 20 |
| Predicted: similar to RAVER1 | 55648233 | RLLpSPLSSA | HLA-A2.1 | 21 |
| SRp46 splicing factor | 14141201 | SMpTRSPPRV | HLA-A2.1 | 22 |
| Adenosine monophosphate deaminase 2 (isoform L) | 56206061 | RQIpSQDVKL | HLA-A2.1 | 23 |
| B lymphocyte signal transduction gene | 4261606 | RQApSIELPSM | HLA-A2.1 | 24 |
| B lymphocyte signal transduction gene | 4261606 | RQApSIELPSMAV | HLA-A2.1 | 25 |
| Carcinoembryonic antigen 2b | 3702267 | SLLTFWNL | HLA-A2.1 | 26 |
| SLTP004 | 20146522 | KVQVpTSLSV | HLA-A2.1 | 27 |
| Tsg24 protein | 11967711 | VLLpSPVPEL | HLA-A2.1 | 28 |
| YME1-like 1, isoform 2 | 14043646 | RLQpSTSERL | HLA-A2.1 | 29 |
| FLJ22624 protein | 55661789 | TLApSPSVFKST | HLA-A2.1 | 30 |
| Premature ovarian failure, 1B | 57284143 | RTYpSGPMNKV | HLA-A2.1 | 31 |
| Serine/threonineprotein kinase Chk1. | 7531055 | KLIDIVpSSQKV | HLA-A2.1 | 32 |
| Desmuslin, synemin | 20137613 | RTFpSPTYGL | HLA-A2.1 | 33 |
| FLJ20297 protein, KIAA1418 protein | 40674045 | ALYpSPAQPSL | HLA-A2.1 | 34 |
| Adenosine monophosphate deaminase 2 (isoform L) | 56206061 | RQIpSQDVKL | HLA-A2.1 | 35 |

TABLE 1-continued

Cancer Antigen Phosphopeptides

| Protein | Gi number | Sequence | HLA type | SEQ ID |
|---|---|---|---|---|
| BRD4_Human bromodomain containing protein 4 | 20141192 | AVVpSPPALHNA | HLA-A2.1 | 36 |
| MUM-2 | 20177848 | RLDpSYVRS | HLA-A2.1 | 37 |
| Pro-apoptotic protein/BCL2adenovirus E1B interacting protein 3like/My020 protein | | HPKRSVpSL | HLA-B7 | 38 |
| KIAA1187/FLJ10350/ Hypothetical protein | | LPApSPRARL | HLA-B7 | 39 |
| FLJ11029 protein/unnamed protein | | HPRpSPTPTL | HLA-B7 | 40 |
| signal-induced proliferation-associated 1 like 1/high-risk human papilloma viruses E6 oncoproteins targeted protein | | YPSpSPRKAL | HLA-B7 | 41 |
| Paternally expressed gene 10 ORF1 | | KPRpsPPRAL | HLA-B7 | 42 |
| Novel protein/similar to cdc42 GTPase activating protein | | RPAKpSMDSL | HLA-B7 | 43 |
| Beta-adrenergic-receptor kinase | | KPRpsPVVEL | HLA-B7 | 44 |
| No direct database hit- (X = L/I) | | RSRpSPRPA(L/I) | HLA-B7 | 45 |
| Suppressor of cytokine signaling protein | | APRpSPPPSRP | HLA-B7 | 46 |
| inositol 1,4,5- triphosphate receptor, type 1 | | RPSGRREpSL | HLA-B7 | 47 |
| Tumor necrosis factor receptor superfamily, member 8 (CD30 antigen) | | RPRRpSSTQL | HLA-B7 | 48 |
| LIM domain only 6 | | RPRpSPPPRAP | HLA-B7 | 49 |
| General transcription factor 2-I | | RPRpSPGSNSKV | HLA-B7 | 50 |
| Ajuba (a novel LIM protein required for mitotic commitment) | | GAQPGRHpSV | HLA-B7 | 51 |
| novel retinal pigment epithelial cell protein/retinoic acid induced 14 | | SPRpSITSTP | HLA-B7 | 52 |
| latent transforming growth factor-beta- binding protein-2 | | KARpSPGRAL | HLA-B7 | 53 |
| No direct database hit- (X = L/I) | | SPRpSPGRS(L/I) | HLA-B7 | 54 |
| TGFB-induced factor 2/TGIF2 | | LPRGSpSPSVL | HLA-B7 | 55 |

TABLE 1 -continued

Cancer Antigen Phosphopeptides

| Protein | Gi number | Sequence | HLA type | SEQ ID |
|---|---|---|---|---|
| DNA directed RNA polymerase I 135 kDa polypeptide/POLR1B protein | | FPHpSLLSVI | HLA-B7 | 56 |
| thyroid hormone receptor associated protein 3 | | SPRERpSPAL | HLA-B7 | 57 |
| RhoGAP protein/Nadrin | | APRRYpSSSL | HLA-B7 | 58 |
| Synemia/desmuslin | | RTFpSPTYGL | HLA-B7 | 59 |
| numb homolog (*Drosophila*)-like | | SPFKRQLpSL | HLA-B7 | 60 |
| Chromatin assembly factor 1, subunit A (p150) | | SPRSPpSTTYL | HLA-B7 | 61 |
| No direct database hit- (X = L/I)-MIX? | | RPApSP(K/Q)RA (K/Q)(L/I) | HLA-B7 | 62 |
| Interleukin enhancer- binding factor 3 (Nuclear factor of activated T-cells 90 kDa) | 62512150 | KLFPDpTPLAL | HLA-A2.1 | 63 |
| Predicted: similar to RAVER1 | 55648233 | RLLpSPLSSA | HLA-A2.1 | 64 |
| MUM-2 (truncated) | 20177848 | RLDpSYVR | HLA-A2.1 | 65 |
| B lymphocyte signal transduction gene | 4261606 | RQApSIELPSM | HLA-A2.1 | 66 |
| KIAA1328 protein- hypothetical protein | 20521886 | KLMpSPKADVKL | HLA-A2.1 | 67 |
| SRp46 splicing factor | 14141201 | SMpTRSPPRV | HLA-A2.1 | 68 |
| TFIID Transcription initiation factor | 5032155 | RLFpSKELRC | HLA-A2.1 | 69 |

In accordance with one embodiment of the present invention, a purified polypeptide is provided comprising the amino acid sequence of SEQ ID NO: 70-171, or an amino acid sequence that differs from any of those sequences by one or more conservative amino acid substitutions. In another embodiment the purified polypeptide comprises an amino acid sequence that differs from SEQ ID NO: 70-171 by less than 5 conservative amino acid substitutions, and in a further embodiment, by 2 or less conservative amino acid substitutions. In accordance with one embodiment of the present invention, a purified polypeptide is provided comprising the amino acid sequence of SEQ ID NO: 70-171, or a bioactive fragment of SEQ ID NO: 70-171, or an amino acid sequence that differs from SEQ ID NO: 70-171 by one to ten conservative amino acid substitutions. In one aspect, a peptide of the invention is an unphosphorylated peptide having a sequence identical with, or highly homologous with, one of the peptides having SEQ ID NOs:70-171. The present invention is also directed to isolated nucleic acids, which comprise nucleic acid sequences encoding the non-phosphorylated homologs of the phosphopeptides of the invention. The polypeptides of the present invention may include additional amino acid sequences to assist in the stabilization and/or purification of recombinantly produced polypeptides. These additional sequences may include intra- or inter-cellular targeting peptides or various peptide tags known to those skilled in the art. In one embodiment, the purified polypeptide comprises an amino acid sequence selected from the group consisting of SEQ ID NO: 70-171 and a peptide tag, wherein the peptide tag is linked to the phosphorylated peptide sequence. Suitable expression vectors for expressing such fusion proteins and suitable peptide tags are known to those skilled in the art and commercially available. In one embodiment the tag comprises a His tag. In another embodiment, the present invention is directed to a purified polypeptide that comprises an amino acid fragment of a phosphorylated polypeptide.

More particularly the phosphorylated polypeptide fragment consists of natural or synthetic portions of a full-length polypeptide selected from the group consisting of SEQ ID NO: 70-171 that are capable of specific binding to their natural ligand. Alternatively, the fragment may comprise an antigenic fragment, including fragments of 10-30, 12-19, 8-12 or 9 amino acids in length, of a polypeptide selected from the group consisting of SEQ ID NO: 70-171.

In accordance with one embodiment, a composition is provided for inducing an immune response against a cancer-associated phosphopeptide as described herein. In one embodiment, the composition consists of a peptide comprising a sequence selected from the group consisting of SEQ ID NO: 70-171, and antigenic fragments of those sequences. The compositions can be combined with a pharmaceutically acceptable carrier or adjuvant and administered to a mammalian species to induce an immune response. The immune response can take the form of an antibody response, a T helper response, or a CTL response. The immune response may be generated in vitro or in vivo.

In accordance with one embodiment, the peptides can be used to immunize a non-human recipient such as a mouse, rat, or goat for the production of antibodies that specifically recognize the peptides. Antibodies to peptides may be generated using methods that are well known in the art. In one embodiment, recombinantly produced peptides, or fragments thereof are used to generate antibodies against the phosphorylated peptides.

In accordance with one embodiment, an antibody is provided which binds to a polypeptide of the invention. In one aspect, the polypeptide is selected from the group consisting of SEQ ID NOs: 70-171. In one embodiment the antibody is a monoclonal antibody. The antibodies may be used with or without modification, and may be labeled by joining them, either covalently or non-covalently, with a reporter molecule. In addition, the antibodies can be formulated with standard carriers and optionally labeled to prepare therapeutic or diagnostic compositions.

Antibodies to peptides may be generated using methods that are well known in the art. For the production of antibodies, various host animals, including rabbits, mice, rats, goats and other mammals, can be immunized by injection with a peptide. They may be conjugated to carrier proteins such as KLH or tetanus toxoid. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Methods of immunization to achieve a polyclonal antibody response are well known in the art, as are the methods for generating hybridomas and monoclonal antibodies.

For preparation of monoclonal antibodies, any technique, which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for epitopes of TAG polypeptides together with genes from a human antibody molecule of appropriate biological activity can be used; such antibodies are within the scope of this invention.

Antibodies generated in accordance with the present invention may include, but are not limited to, polyclonal, monoclonal, chimeric (i.e., "humanized" antibodies), single chain (recombinant), Fab fragments, and fragments produced by a Fab expression library. These antibodies can be used as diagnostic agents for the diagnosis of conditions or diseases characterized by expression or overexpression of antigen peptides (such as cancer), or in assays to monitor a patients responsiveness to an anti-cancer therapy. In one embodiment antibodies specific for one or more of the antigen peptides are used as diagnostics for the detection of the antigen peptides in cancer cells.

The antibodies or antibody fragments of the present invention can be combined with a carrier or diluent to form a composition. In one embodiment, the carrier is a pharmaceutically acceptable carrier. Such carriers and diluents include sterile liquids such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose, and related sugar solution, and glycols such as, propylene glycol or polyethylene glycol, are preferred liquid carriers, particularly for injectable solutions.

In accordance with one embodiment, the detection of antigen peptides is used as a diagnostic mark for detecting cancer. In another embodiment the antigen peptides can be used to immunize an individual to induce an immune response. The induced response may include T helper cells or CTL specific for the antigen peptides. The induced immune response may be useful in preventing the development of cancer in an individual without cancer, and it may be useful in eliminating or preventing the further spread of the disease in an individual with cancer. In one embodiment the antigen peptides may be added to antigen presenting cells. The antigen presenting cells will now present antigen peptides, which can be used to stimulate an in vitro T helper cell or CTL response. The T helper cells or CTL can then be used as diagnostics to detect the presence of tumor cells. The T helper cells or CTL can also be infused into a cancer patient as a treatment for cancer.

Accordingly, one embodiment of the invention is directed to the use of antigen peptides as diagnostic markers for neoplastic disease such as cancer. The method comprises the steps of screening for elevated levels or inappropriate expression of antigen peptides, including the expression of antigen peptides in somatic tissues. The term "inappropriate expression" includes any non-typical expression that is deleterious to the cell or host organism, including for example, expression in a cell type that normally does not express the peptide, or expression of a modified form of the peptide that impacts cell function. Such screens could be conducted using antibodies specific for the antigen. Alternatively, antibodies directed against antigen peptides can be used in assays to monitor patients being treated with anti-cancer therapies to monitor the effectiveness of the therapy.

The antigen peptides are known to be expressed in melanoma, ovarian, breast, colorectal, or squamous carcinoma of the lung, and thus may be used as immunogens to prevent, eliminate, or delay the progression of, inter alia, these types of cancer.

In one aspect, the cancer is, inter alia, sarcoma, renal cell carcinoma, pancreatic carcinomas, squamous tumors of the head and neck.

These same antigen peptides may also be expressed in untested forms of cancer and thus may be useful in their ability to prevent, eliminate, or delay the progression of additional cancers.

Antibodies generated with specificity for the antigen peptides are used in accordance with one embodiment to detect the corresponding peptides in biological samples. The biological sample could come from an individual whom is suspected of having cancer and thus detection would serve to diagnose the cancer. Alternatively, the biological sample may come from an individual known to have cancer, and detection of the antigen peptides would serve as an indicator of disease prognosis or treatment efficacy. Appropriate immunoassays are well known in the art and include, but are not limited to, immunohistochemistry, flow cytometry, radioimmunoassay, western blotting, and ELISA. Biological samples suitable for such testing would include, but are not limited to, cells, tissue biopsy specimens, whole blood, plasma, serum, sputum, cerebrospinal fluid, pleural fluid, and urine.

Antigens recognized by T cells, whether helper T lymphocytes or CTL, are not recognized as intact proteins, but rather as small peptides that associate with class I or class II MHC proteins on the surface of cells. During the course of a naturally occurring immune response antigens that are recognized in association with class II MHC molecules on antigen presenting cells are acquired from outside the cell, internalized, and processed into small peptides that associate with the class II MHC molecules. Conversely, the antigens that give rise to proteins that are recognized in association with class I MHC molecules are generally proteins made within the cells, and these antigens are processed and associate with class I MHC molecules. It is now well known that the peptides that associate with a given class I or class II MHC molecule are characterized as having a common binding motif, and the binding motifs for a large number of different class I and II MHC molecules have been determined. It is also well known that synthetic peptides can be made which correspond to the sequence of a given antigen and which contain the binding motif for a given class I or II MHC molecule. These peptides can then be added to appropriate antigen presenting cells, either in vitro or in vivo, and be used to stimulate a T helper cell or CTL response. The binding motifs, methods for synthesizing the peptides, and methods for stimulating a T helper cell or CTL response are all well known and readily available.

The antigens of this invention may take the form of antigen peptides added to autologous dendritic cells and used to stimulate a T helper cell or CTL response in vitro. The in vitro generated T helper cells or CTL can then be infused into a patient with cancer (Yee et al., 2002), and specifically a patient with a form of cancer that expresses one or more of antigen peptides. The antigen peptides may also be used to vaccinate an individual. The antigen peptides may be injected alone, but most often they would be administered in combination with an adjuvant. The proteins may also be added to dendritic cells in vitro, with the dendritic cells being subsequently transferred into an individual with cancer with the intent of stimulating an immune response.

Peptide analogs can readily be synthesized that retain their ability to stimulate a particular immune response, but which also gain several beneficial features which include, but are not limited to the following: (i) Substitutions may be made in the peptide at residues known to interact with the MHC molecule. Such substitutions can have the effect of increasing the binding affinity of the peptide for the MHC molecule and can also increase the lifespan of the peptide-MHC complex, the consequence of which is that the analog is a more potent stimulator of an immune response than is the original peptide. (ii) The substitutions may be at positions in the peptide that interact with the receptor on the T helper cells or CTL, and have the effect of increasing the affinity of interaction such that a stronger immune response is generated. (iii) Additionally, the substitutions may have no effect on the immunogenicity of the peptide per se, but rather than may prolong its biological half-life or prevent it from undergoing spontaneous substitutions or alternations which might otherwise negatively impact on the immunogenicity of the peptide.

The antigen peptides of this invention can also be used as a vaccine for cancer, and more specifically for melanoma, ovarian, breast, colorectal, or lung squamous cancer. The antigens may take the form of genes, proteins, or peptides. The vaccine may include only the antigens of this invention or they may include other cancer antigens that have been identified. Pharmaceutical carriers, diluents and excipients are generally added that are compatible with the active ingredients and acceptable for pharmaceutical use. Examples of such carriers include, but are not limited to, water, saline solutions, dextrose, or glycerol. Combinations of carriers may also be used. The vaccine compositions may further incorporate additional substances to stabilize pH, or to function as adjuvants, wetting agents, or emulsifying agents, which can serve to improve the effectiveness of the vaccine.

The composition may be administered parenterally or orally, and, if parenterally, either systemically or topically. Parenteral routes include subcutaneous, intravenous, intradermal, intramuscular, intraperitoneal, intranasal, transdermal, or buccal routes. One or more such routes may be employed. Parenteral administration can be, for example, by bolus injection or by gradual perfusion over time. Alternatively, or concurrently, administration may be by the oral route.

It is understood that the suitable dosage of an immunogen of the present invention will depend upon the age, sex, health, and weight of the recipient, the kind of concurrent treatment, if any, the frequency of treatment, and the nature of the effect desired, however, the most preferred dosage can be tailored to the individual subject, as determined by the researcher or clinician. The total dose required for any given treatment will commonly be determined with respect to a standard reference dose based on the experience of the researcher or clinician, such dose being administered either in a single treatment or in a series of doses, the success of which will depend on the production of a desired immunological result (i.e., successful production of a T helper cell and/or CTL-mediated response to the antigen, which response gives rise to the prevention and/or treatment desired). Thus, the overall administration schedule must be considered in determining the success of a course of treatment and not whether a single dose, given in isolation, would or would not produce the desired immunologically therapeutic result or effect. Thus, the therapeutically effective amount (i.e., that producing the desired T helper cell and/or CTL-mediated response) will depend on the antigenic composition of the vaccine used, the nature of the disease condition, the severity of the disease condition, the extent of any need to prevent such a condition where it has not already been detected, the manner of administration dictated by the situation requiring such administration, the weight and state of health of the individual receiving such administration, and the sound judgment of the clinician or researcher. Needless to say, the efficacy of administering additional doses, and of increasing or decreasing the interval, may be re-evaluated on a continuing basis, in view of the recipient's immunocompetence (for example, the level of T helper cell and/or CTL activity with respect to tumor-associated or tumor-specific antigens).

The concentration of the T helper or CTL stimulatory peptides of the invention in pharmaceutical formulations are subject to wide variation, including anywhere from less than 0.01% by weight to as much as 50% or more. Factors such as volume and viscosity of the resulting composition should also be considered. The solvents, or diluents, used for such compositions include water, possibly PBS (phosphate buffered saline), or saline itself, or other possible carriers or excipients. The immunogens of the present invention may also be contained in artificially created structures such as liposomes, which structures may or may not contain additional molecules, such as proteins or polysaccharides, inserted in the outer membranes of said structures and having the effect of targeting the liposomes to particular areas of the body, or to particular cells within a given organ or tissue. Such targeting molecules may commonly be some type of immunoglobulin. Antibodies may work particularly well for targeting the liposomes to tumor cells.

The present invention is also directed to a vaccine in which a peptide or polypeptide or active fragment of the present invention is delivered or administered in the form of a polynucleotide coding the peptide or polypeptide or active fragment, whereby the peptide or polypeptide or active fragment is produced in vivo. The polynucleotide may be included in a suitable expression vector and combined with a pharmaceutically acceptable carrier.

The vaccine compositions may be used prophylactically for the purposes of preventing cancer in an individual that does not currently have cancer, or they may be used to treat an individual that already has cancer. Prevention relates to a process of prophylaxis in which the individual is immunized prior to the induction or onset of cancer. For example, individuals with a history of severe sunburn and at risk for developing melanoma, might be immunized prior to the onset of the disease. Alternatively, individuals that already have cancer can be immunized with the antigens of the present invention so as to stimulate an immune response that would be reactive against the cancer. A clinically relevant immune response would be one in which the cancer partially or completely regresses and is eliminated from the patient, and it would also include those responses in which the progression of the cancer is blocked without being eliminated.

In one embodiment, the present invention provides methods of screening for agents, small molecules, or proteins that interact with polypeptides comprising a sequence selected from the group consisting of SEQ ID NO: 1 through 69 or bioactive fragments thereof. The invention encompasses both in vivo and in vitro assays to screen small molecules, compounds, recombinant proteins, peptides, nucleic acids, antibodies, etc., which bind to or modulate the activity of antigen peptides and are thus useful as therapeutic or diagnostic markers for cancer. As used herein, modulating the activity of an antigen peptide includes interfering or altering the antigen peptide ligand binding properties.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Example 1

Phosphorylated peptides were extracted from melanoma cell lines that express either or both of HLA-B7 and HLA-A*0201, identified by mass spectrometry to be differentially displayed on melanoma versus a control B cell line, and then sequenced. The peptides were identified through the following procedure. Two melanoma cell lines and one B lymphoblastoid cell line were extracted with detergent containing buffer, and HLA-A*0201 class I MHC molecules were purified by immunoaffinity chromatography. Peptides were separated from the MHC molecules by extraction in acid and filtration through a 5000 dalton cut-off filter. Phosphopeptides were identified through analysis by microcapillary reversed phase high performance liquid chromatography tandem mass spectrometry. Sequences were determined from an analysis of collision activated dissociation spectra. Source proteins were determined from a search of protein and DNA databases. SEQ ID NOs:1 through 69 were identified (see Table 1). One of ordinary skill in the art would appreciate that such techniques can be modified and that other techniques are known to aid in identifying peptides of the invention.

These peptides represent potential targets of an immune response, either cytotoxic T lymphocyte or antibody, that could be used for either therapeutic or diagnostic purposes. While the peptides have been identified on melanoma cells, they may also be expressed on other kinds of cancer cells and the invention covers their use for cancers other than melanoma. The binding of these peptides to class I MHC molecules is necessary for their recognition by cytotoxic T lymphocytes, while recognition by antibody could occur in either a class I MHC associated or free form. The invention comprises these peptides, together with structural modifications that retain or enhance the ability: 1) to bind to MHC molecules or; 2 to stimulate an immune response or; 3 to be recognized by a product of an immune response.

The binding of the peptides to class I MHC molecules can be determined by 2-3 anchor residues within the sequence, and these peptides are generally 8-11 residues in length. For example, peptides that bind to HLA-B7 generally contain a Pro at the second position, a hydrophobic aliphatic residue at the carboxyl terminus, and are 9 residues long. However, some peptides have been identified that do not contain one of these anchor residues, and peptides up to 14 residues in length have also been identified. It has also been shown that other residues in a sequence may augment or diminish binding, despite the presence or absence of appropriate anchor residues.

The sequences displayed on a cell are derived from proteolysis of proteins made inside the cell and transported into the lumen of the endoplasmic reticulum. The specificities of the proteases and the transporter are poorly understood, and the sequences of all proteins made by human cells, based on data from the Human Genome Project, are very incomplete. In addition, proteins may undergo modifications such as phosphorylation. However, relatively few of these sites have been identified. Thus, there is a large universe of potential peptides displayed by any given MHC molecule based on the sequences of all proteins made by the cell and the distribution of appropriate anchor motifs within those sequences. However, the exact peptides displayed by a cell are not readily predictable. The direct identification of such peptides by mass spectrometry provides information that cannot be otherwise obtained at present without undue effort.

Different MHC molecules may have similar anchor preferences, leading to the possibility that a peptide associated with, for example, HLA-A*0201, may also be displayed by HLA-A3. The existence of such "supertypes" means that the peptides identified above in association with one MHC molecule may be presented by others, broadening their utility as antigens.

Example 2

Figure 1B:
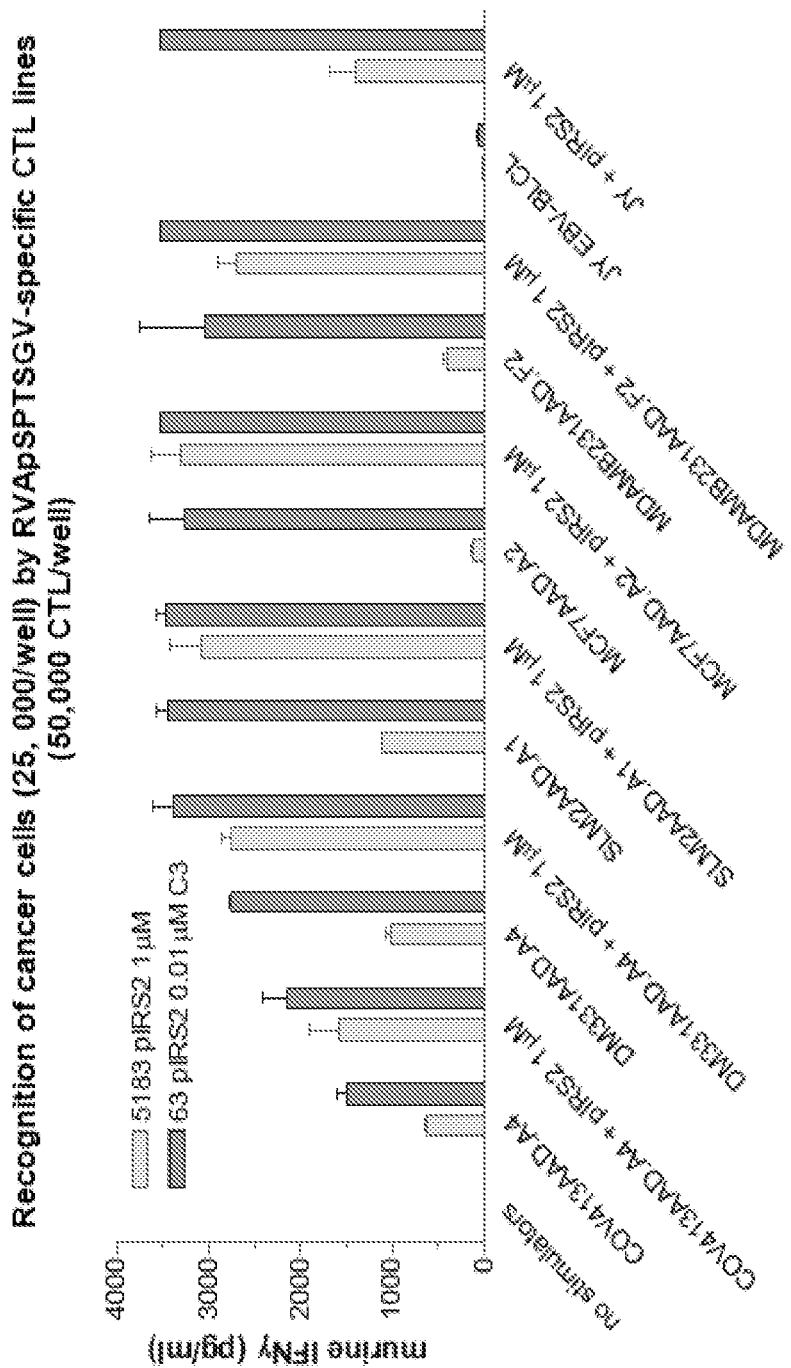

CTL specific for two of the antigen peptides were generated by long term culture with the peptides. Two CTL lines specific for the antigen peptide GLLGpSPVRA, lines 6850 and 6960, SEQ ID NO: 13, and two CTL lines specific for the antigen peptide RVApSPTSGV, SEQ ID NO: 14, lines 5183 and 63 were used to detect these two antigen peptides on cancer cells. The phosphopeptide-specific CTL (50,000 CTL/well) were incubated 24 hours with the following cancer cell lines or EBV-transformed B lymphoblastoid cell lines (BLCL) (25,000 cells/well): COV413.AAD.A4 ovarian carcinoma, DM331.AAD.A4 and SLM2.AAD.A1 melanomas, MCF7.AAD.A2 and MDAMB231.AAD breast carcinomas, and JY EBVBLCL. Supernatants were harvested 24 hours later and evaluated for the presence of murine IFN☐ (produced by murine CTL lines) by ELISA (eBioscience Ready-Set-go murine IFN☐ ELISA kit). As a positive control, cancer cells were pulsed with the specific antigen peptide (1 ☐M) to show that they are capable of presenting exogenously added peptide. In FIG. 1A, two phosphopeptide-specific CTL cell lines, 6850 and 6960, specific for the phosphopeptide GLLGpSPVRA, recognize the phosphopeptide on all the cancer cell lines, but not the control cell line. In FIG. 1B, two phosphopeptide-specific CTL cell lines, 5183 and 63, specific for the phosphopeptide RVApSPTSGV, recognize the phosphopeptide on all the cancer cell lines, but not the control cell line.

Example 3

Over-expression of select phospho-proteins is a hallmark of malignant transformation.

Due to the low expression levels of phosphopeptides by the MHC class I pathway, identification of immunologically relevant phospho-peptides is difficult.

Secreted MHC molecule technology allows for an increase in the amounts of MHC class I peptides available for analysis.

Identification of MHC class I phosphopeptides that are unique to tumor cells provides an avenue to the production of peptide-based cancer vaccines and biomarkers Materials, Methods, and Results Table 2 as set forth in FIG. 2 presents phosphopeptides of the present invention on breast cancer by the Class I MHC Molecule, in particular, on the HLA B*0702 allele. Table 3, as set forth below, summarizes "Source proteins for peptides identified from analyses of samples from breast cancer and immortalized cell lines and their expression in non-tumorigenic control cell line 184B5 and the breast cancer cell lines BT20 and MCF-7".

Figure 3:
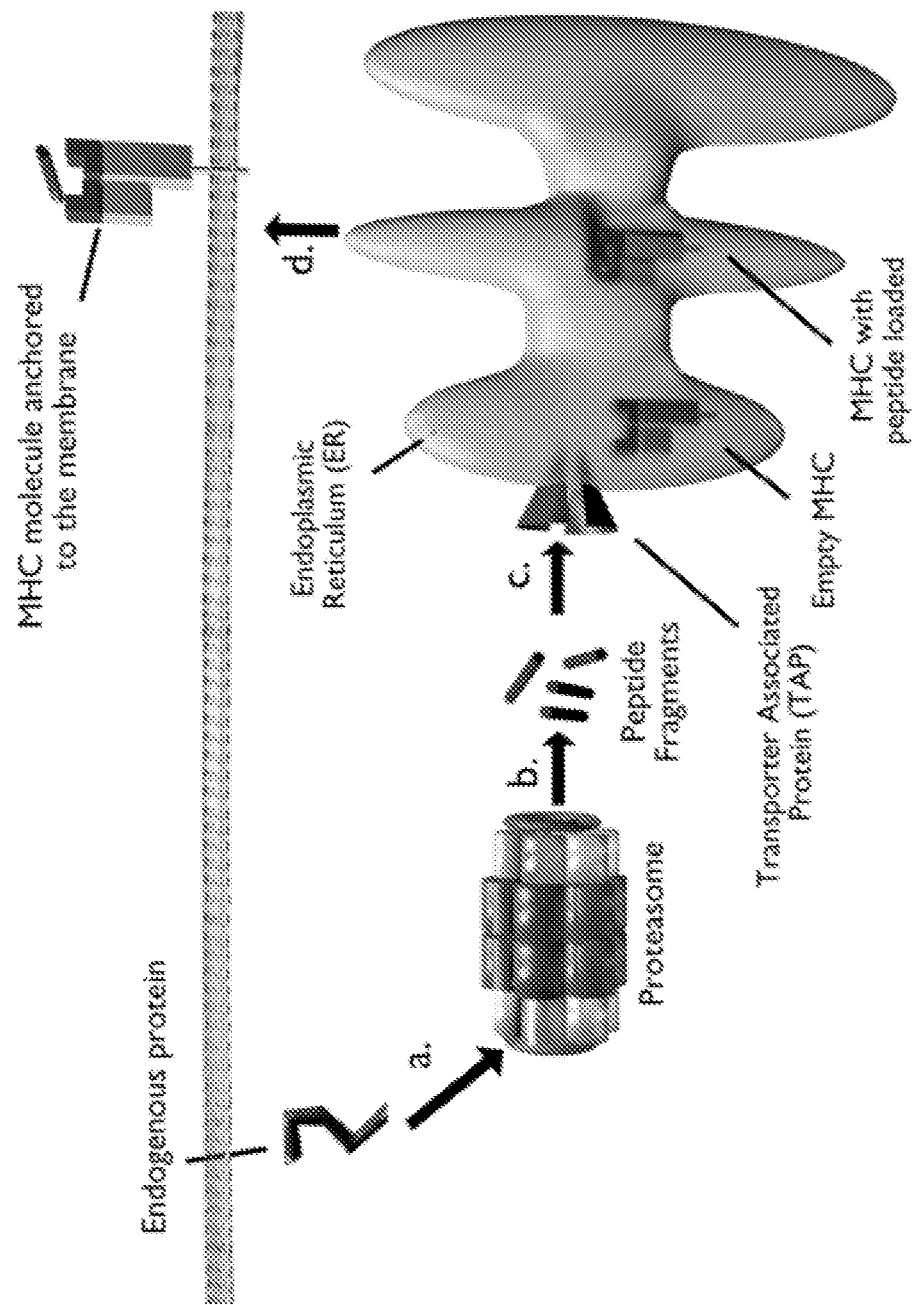
FIG. 3 graphically demonstrates the MHC class I pathway.
Figure 4:
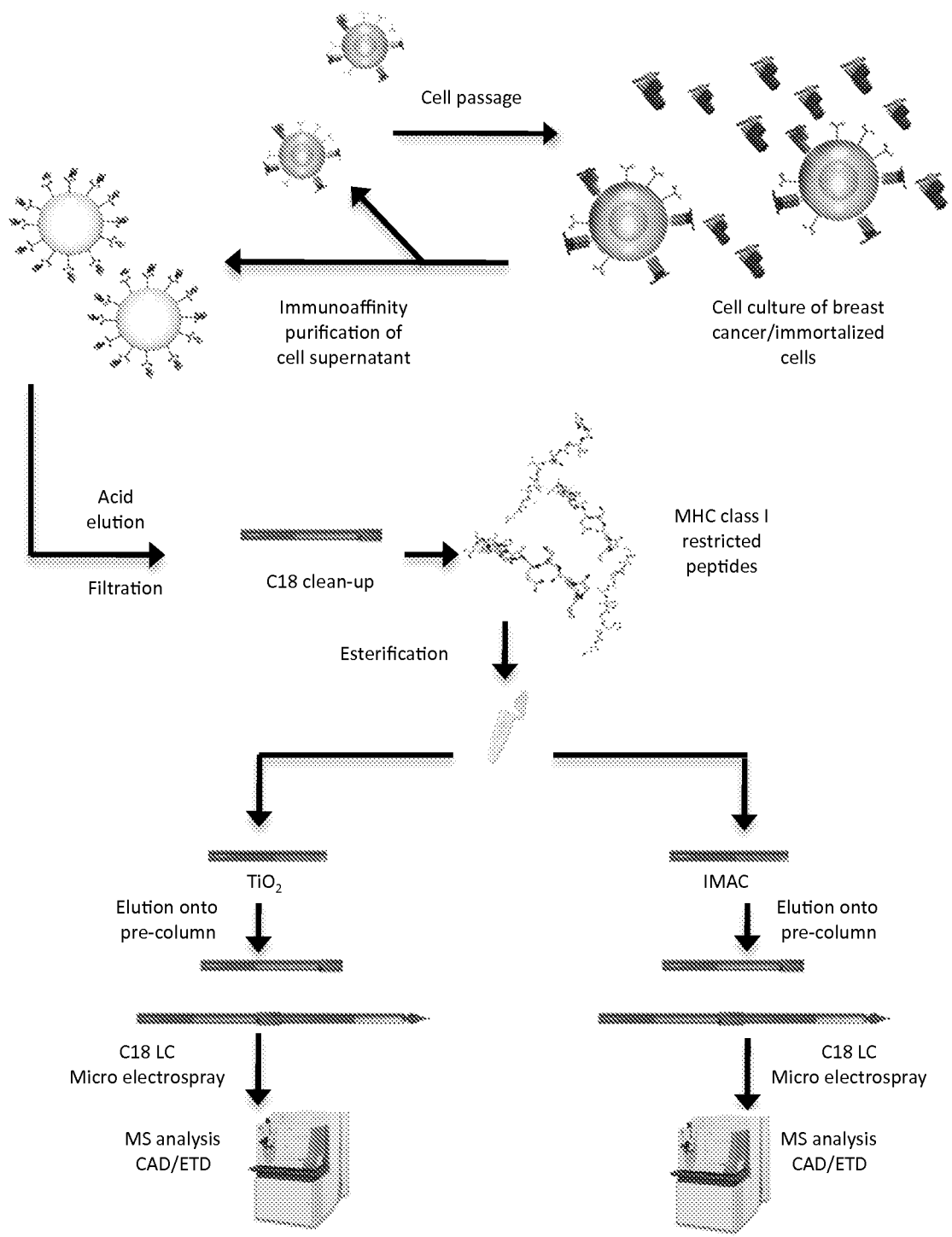
FIG. 4 schematically illustrates an overview of sample analysis.

FIG. 3 graphically demonstrates
The MHC class I pathway—
a) Protein is marked for degradation
b) The proteasome digests the peptides into smaller fragments
c) Peptides are transported into the ER via the transporter associated protein (TAP)
d) The MHC molecule with peptide loaded is transported to the surface FIG. 4 schematically illustrates "Sample analysis overview. Cells are grown in culture and the cell supernatant is collected. MHC molecules are immunoaffinity purified and peptides are eluted under acidic conditions. Peptides are esterified, enriched for phospho-peptides through IMAC and/or TiO2 and analyzed via C18 micro electrospray LC/MS with high resolution full MS and low resolution MS/MS".

Figures 5, 6:
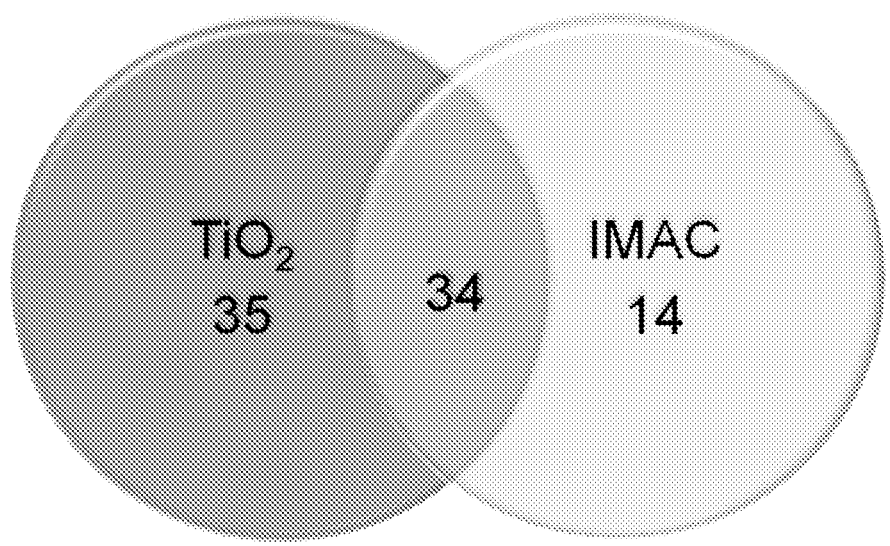
FIG. 5 describes the B*0702 motif showing amino acid anchors.
FIG. 6 shows the total number of peptides in IMAC and TiO2 experiments and schematically depicts the overlap between the peptides identified in an IMAC analysis of 184B5 and a TiO2 analysis.

FIG. 5 describes the B*0702 motif showing amino acid anchors.

FIG. 6 shows the total number of peptides in IMAC and TiO2 experiments and schematically depicts the overlap between the peptides identified in an IMAC analysis of 184B5 and a TiO2 analysis. The IMAC analysis was performed twice, once with ETD fragmentation (d.d. top 6) and once with CAD (d.d. top 10) fragmentation. The TiO2 analysis was performed in a single run with toggled ETD/CAD fragmentation. We investigated each MS analysis for the presence of all identified sequences using the calculated accurate mass value.

The MHC class I pathway (FIG. 3) is classically responsible for presenting endogenous peptides to the immune system. Each MHC molecule has a binding pocket which can only accept peptides with narrowly defined motifs. The MHC molecule with peptide loaded in the binding groove is transported to the surface where the MHC molecule remains anchored to the membrane Phospho-peptides can be processed and displayed by the MHC class I pathway.

Secreted MHC Molecules
  A cDNA clone of a specific MHC molecule is altered to remove the regions that code for the transmembrane and cytoplasmic portions of the protein
  Cloned into a plasmid expression vector
  Cell produce endogenous MHC molecules as well as the secreted MHC molecules (sHLA)
  sHLA are released into the cell culture medium as they lack the portion of the protein responsible for anchoring them to the membrane
  The inventors have demonstrated that sHLA molecules successfully present phospho-peptides and that they display a similar repertoire of phospho-peptides as endogenous HLA molecules.
Phosphopeptide Analyses
  Breast cancer cell lines (BT20, MCF7) and an immortalized non-malignant mammary tissue cell line (184B5) were transfected with the B*0702 sHLA cDNA1
  FIG. 5 shows the motif for peptides which are presented by B*0702 MHC molecules
  Samples were analyzed with both ETD fragmentation and CAD fragmentation on either an Orbitrap or FT-ICR instrument, which were in-house custom modified for front end electron transfer dissociation Species of interest were identified by a combination of algorithm searching (OMSSA), d0/d3 methyl ester pair detection and CAD neutral loss detection Peptide sequences were determined by manual confirmation of search data and de novo sequencing utilizing both CAD and ETD data where necessary Source proteins were determined by BLAST2 search, and a single protein identification was determined from UniProt 3

Due to issues with non-specific binding having a negative effect on the ability to identify peptides in IMAC experiments, TiO2 was considered as an alternative. FIG. 4 shows the total number of peptides in IMAC and TiO2 experiments. The level of non-specific binding for non-phospho peptides was reduced substantially in the TiO2 experiment, however recovery of the angiotensin II phosphate (DRVy-IHPF) standard peptide was much lower in the TiO2 experiment.

Conclusions—Example 3

104 phospho-peptides have been identified, deriving from 84 different source proteins 22 phospho-peptides were only detected in samples deriving from breast cancer cell lines 2 peptides were identified in both cancer cell lines but not in the control cell line Peptides from source proteins known to be involved in tumors have been identified In a complementary TiO2/IMAC experiment, 34 peptides were common to both analyses, 14 peptides were unique to the IMAC experiment and 35 peptides were unique to the TiO2 experiment Based on the disclosure provided herein, the present invention encompasses compositions and methods useful for submitting/testing specific peptides of immunological interest for binding and T-cell recognition assays. The present invention further encompasses compositions and methods to apply the sHLA technology to cell lines with known phospho-peptide expression patterns and the present invention has application to cells with non-ideal HLA alleles and/or cells with poor growth.

BIBLIOGRAPHY

1. Oriana E. Hawkins, Rodney S. VanGundy, Annette M. Eckerd, Wilfried Bardet, Rico Buchli, Jon A. Weidanz, and William H. Hildebrand, Journal of Proteome 10 Research, 2008, 7, 1445-1457.
2. Altschul S F; Gish W; Miller W; Myers E W; Lipman D J, Journal of Molecular Biology, 1990, 215, 403-410.
3. The UniProt Consortium, The Universal Protein Resource (UniProt) in 2010, Nucleic Acids Research, 2010, D142-D148 15

TABLE 3

| Uniprot protein identification | 184B5 | BT20 | MCF7 | Uniprot protein identification | 184B5 | BT20 | MCF7 |
|---|---|---|---|---|---|---|---|
| A-kinase anchor protein 13 | X | X | | Unique peptide, unidentified source 6 | X | X | X |
| Ankycorhin | X | | | Unique peptide, unidentified source 7 | X | | |
| Arginine-glutamic acid dipeptide repeats protein | | X | | Unique peptide, unidentified source 8 | X | X | |
| Ataxin-2 | X | X | X | Neuron navigator 1 | X | | |
| Ataxin-2-with point mutation | X | X | | Nuclear factor erythroid 2-related factor 1 | X | | |
| Ataxin-2-like protein | X | X | | Nuclear receptor coactivator 1 | X | | X |
| AT-rich interactive domain-containing protein 1A | X | X | | Numb-like protein | X | X | X |
| Beta-adrenergic receptor kinase 1 | X | X | X | Partner and localizer of BRCA2 | | X | |
| Butyrate response factor 2 | X | X | | Phosphatidylinositol 4,5-bisphosphate 5phosphatase A | | X | |
| Cdc42-interacting protein 4 | X | X | | Plakophilin-3 | X | X X | |
| Centrosomal protein of 55 kDa | X | X | | Plakophilin-3 | X | | |
| Chondroitin Sulfate synthase 2 | | X | | Plakophilin-3 | X | | |
| Chromatin assembly factor 1subunit A | X | | X | Pleckstrin homology domain-containing family G | X | | |
| Coiled-coil domain-containing protein 6 | | X | X | Pleckstrin homology-like domain family B member 1 | | X | |
| Cullin-4A | X | X | | Proline-rich protein 11 | | | X |
| Death-associated protein kinase 1 | X | | | proteasome non-ATPase regulatory subunit 4 | X | | |
| DENN domain-containing protein 4C | | X | | Protein AF-17 | X | | |
| DNA replication factor Cdt1 | X | | | Protein ajuba | X | | |

TABLE 3-continued

| Uniprot protein identification | 184B5 | BT20 | MCF7 | Uniprot protein identification | 184B5 | BT20 | MCF7 |
|---|---|---|---|---|---|---|---|
| DNA-binding protein inhibitor ID-2 | X | | | Protein TANC2 | X | X | |
| DNA-directed RNA polymerase I subunit RPA2 | | X | | Putative phosphoserine phosphatase-like protein | X | | |
| Dyamin-1-like protein | X | | | Rab11 family-interacting protein 1 | X | | |
| E3 ubiquitin-protein ligase NEDD4-like | X | | | Ras-associated and pleckstin homology domains-containing protein 1 | X | | X |
| E3 ubiquitin-protein ligase NEDD4-like | X | | | Ras-like protein family member 11A | X | | X |
| E3 ubiquitin-protein ligase UBR5 | | | | Receptor expression-enhancing protein 4 | | | X |
| Eukaryotic translation initiation factor 4B | | | | Receptor-interacting serine/threonine-protein kinase 4 | | | X |
| General transcription factor II-I | | | | RelA-associated inhibitor | | | X |
| Helicase SKI2W | X | | | Retrotransposon-derived protein PEG10 | X | | X |
| Histone-lysine N-methyltransferase SETD2 | | | | Retrotransposon-derived protein PEG10 | | | X |
| Homeobox protein TGIF2 | X | | | Rho GTPase-activating protein 30 | | | X |
| Hypoxia-inducible factor 1-alpha | | | | Rho GTPase-activating protein 30 | | | X |
| Krueppel-like factor 10 | | | | RNA pseudouridylate synthase domain | | | X |
| Latent-transforming growth factor beta-binding protein 2 | X | | | Serine/arginine repetitive matrix protein 2 | | | X |
| Leucine zipper protein 1 | X | X | X | Serine/threonine-protein kinase SIK1 | X | | X |
| Lipolysis-stimulated lipoprotein receptor | X | X | X | Serine/threonine-protein kinase tousled-like 1 | X | X | |
| MAP7 domain-containing protein 1 | X | X | | Signal-induced proliferation-associated 1-like protein 1 | X | | |
| MICAL-like protein 1 | X | | | Ski oncogene | X | | |
| MICAL-like protein 2 | X | X | | Splicing factor, arginine/serine-rich 7 | X | X | X |
| MICAL-like protein 2 | X | X | | Sterol regulatory element-binding protein | X | X | |
| Microtubule-actin cross-linking factor 1 | X | | | Targeting protein for Xklp2 | | X | |
| Mitogen-activated protein kinase kinase kinase 11 | | X | X | Tensin-4 | X | | |
| Mitogen-activated protein kinase kinase kinase 11 | | X | | Thyroid hormone receptor-associated protein 3 | X | | |
| Myocyte-specific enhancer factor 2D | | X | | Transcription factor HIVEP2 | X | | |
| Myocyte-specific enhancer factor 2D | | X | | Transformer-2 protein homolog beta | | X | |
| Myocyte-specific enhancer factor 2D | X | | | Transient receptor potential cation channel | X | | |
| Myosin regulatory light chain 12A | X | X | | TSC22 domain family protein 4 | X | | |
| Unique peptide, unidentified source 1 | X | | X | Ubiquitin carboxyl-terminal hydrolase 43 | X | | |
| Unique peptide, unidentified source 2 | X | | | Uncharacterized protein C1orf106 | | X | |
| Unique peptide, unidentified source 3 | X | | X | Uncharacterized protein C6orf64 | X | X | |
| Unique peptide, unidentified source 4 | X | | | Uncharacterized protein CXorf66 | X | | |
| Unique peptide, unidentified source 5 | X | | | Uncharacterized protein KIAA0819 | X | | |
| YTH domain-containing | | X | | Uncharacterized protein | X | X | |

TABLE 3-continued

| Uniprot protein identification | 184B5 | BT20 | MCF7 | Uniprot protein identification | 184B5 | BT20 | MCF7 |
|---|---|---|---|---|---|---|---|
| protein 1 | | | | KIAA1310 | | X | |
| Zinc finger protein 335 | X X | | | Yorkie homolog | | X | |

The disclosures of each and every patent, patent application, and publication cited herein are hereby incorporated by reference herein in their entirety. One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described 10 therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

What is claimed is:

1. A composition comprising:
(a) an isolated or synthetic phosphopeptide having a length of 10 to 30 amino acids and comprising a sequence selected from the group consisting of:
SEQ ID NO: 132;
SEQ ID NO: 132 wherein the serine at the fourth position is phosphorylated;
SEQ ID NO: 71 wherein the serine at the fourth position is phosphorylated;
SEQ ID NO: 72 wherein the serine at the eighth position is phosphorylated;
SEQ ID NO: 73 wherein the serine at the sixth position is phosphorylated;
SEQ ID NO: 75 wherein the serine at the sixth position is phosphorylated;
SEQ ID NO: 76 wherein the serine at the eighth position is phosphorylated;
SEQ ID NO: 78 wherein the serine at the sixth position is phosphorylated;
SEQ ID NO: 79 wherein the serine at the fourth position is phosphorylated;
SEQ ID NO: 80 wherein the threonine at the third position is phosphorylated;
SEQ ID NO: 84 wherein the serine at the fourth position is phosphorylated;
SEQ ID NO: 87 wherein the serine at the eighth position is phosphorylated;
SEQ ID NO: 93 wherein the serine at the fourth position is phosphorylated;
SEQ ID NO: 94 wherein the serine at the fifth position is phosphorylated;
SEQ ID NO: 97 wherein the serine at the fourth position is phosphorylated;
SEQ ID NO: 99 wherein the serine at the sixth position is phosphorylated;
SEQ ID NO: 100 wherein the serine at the fourth position is phosphorylated;
SEQ ID NO: 101 wherein the serine at the sixth position is phosphorylated;
SEQ ID NO: 102 wherein the serine at the fourth position is phosphorylated;
SEQ ID NO: 104 wherein the serine at the sixth position is phosphorylated;
SEQ ID NO: 105 wherein the serine at the fourth position is phosphorylated;
SEQ ID NO: 110 wherein the serine at the fourth position is phosphorylated;
SEQ ID NO: 112 wherein the serine at the fourth position is phosphorylated;
SEQ ID NO: 113 wherein the serine at the fourth position is phosphorylated;
SEQ ID NO: 114 wherein the serine at the fourth position is phosphorylated;
SEQ ID NO: 115 wherein the serine at the fourth position is phosphorylated;
SEQ ID NO: 117 wherein the serine at the sixth position is phosphorylated;
SEQ ID NO: 118 wherein the serine at the tenth position is phosphorylated;
SEQ ID NO: 120 wherein the threonine at the fourth position is phosphorylated;
SEQ ID NO: 126 wherein the serine at the sixth position is phosphorylated;
SEQ ID NO: 127 wherein the serine at the sixth position is phosphorylated;
SEQ ID NO: 135 wherein the serine at the sixth position is phosphorylated;
SEQ ID NO: 140 wherein the serine at the fourth position is phosphorylated;
SEQ ID NO: 143 wherein the serine at the fourth position is phosphorylated;
SEQ ID NO: 145 wherein the serine at the fourth position is phosphorylated;
SEQ ID NO: 146 wherein the tyrosine at the fifth position is phosphorylated;
SEQ ID NO: 149 wherein the serine at the fourth position is phosphorylated;
SEQ ID NO: 151 wherein the serine at the eighth position is phosphorylated;
SEQ ID NO: 153 wherein the serine at the seventh position is phosphorylated;
SEQ ID NO: 154 wherein the serine at the fifth position is phosphorylated;
SEQ ID NO: 160 wherein the serine at the fourth position is phosphorylated;
SEQ ID NO: 161 wherein the serine at the fourth position is phosphorylated;
SEQ ID NO: 162 wherein the serine at the fourth position is phosphorylated and the serine at the eighth position is phosphorylated;
SEQ ID NO: 163 wherein the serine at the fourth position is phosphorylated;
SEQ ID NO: 166 wherein the serine at the seventh position is phosphorylated;
SEQ ID NO: 167 wherein the serine at the fourth position is phosphorylated;
SEQ ID NO: 168 wherein the serine at the fourth position is phosphorylated;
SEQ ID NO: 169 wherein the serine at the fourth position is phosphorylated;
SEQ ID NO: 170 wherein the serine at the seventh position is phosphorylated, and
(b) an adjuvant.

2. The composition of claim 1, wherein said composition has the ability to stimulate a T cell mediated immune response to at least one of said phosphopeptides.

3. The composition of claim 1, comprising a peptide capable of binding to the HLA-B*0702 allele on the MHC class I molecule.

4. A method of inducing an immunogenic response comprising administering to a patient in need thereof a therapeutically effective amount of the composition of claim 1.

5. A method of treating cancer comprising administering to a patient in need thereof a therapeutically effective amount of the composition of claim 1.

6. A method of treating breast cancer comprising administering to a patient in need thereof a therapeutically effective amount of the composition of claim 1.

7. The composition of claim 1, wherein the at least one synthetic target peptide comprises the amino acid sequence as set forth in SEQ ID NO: 132.

8. The composition of claim 1, wherein the at least one synthetic target peptide comprises the amino acid sequence as set forth in SEQ ID NO: 132, wherein the serine at the fourth position is phosphorylated.

9. The composition of claim 1, wherein the at least one synthetic target peptide comprises the amino acid sequence as set forth in SEQ ID NO: 71, wherein the serine at the fourth position is phosphorylated.

10. The composition of claim 1, wherein the at least one synthetic target peptide comprises the amino acid sequence as set forth in SEQ ID NO: 72, wherein the serine at the eighth position is phosphorylated.

11. The composition of claim 1, wherein the at least one synthetic target peptide comprises the amino acid sequence as set forth in SEQ ID NO: 73, wherein the serine at the sixth position is phosphorylated.

12. The composition of claim 1, wherein the at least one synthetic target peptide comprises the amino acid sequence as set forth in SEQ ID NO: 75, wherein the serine at the sixth position is phosphorylated.

13. The composition of claim 1, wherein the at least one synthetic target peptide comprises the amino acid sequence as set forth in SEQ ID NO: 76, wherein the serine at the eighth position is phosphorylated.

14. The composition of claim 1, wherein the at least one synthetic target peptide comprises the amino acid sequence as set forth in SEQ ID NO: 78, wherein the serine at the sixth position is phosphorylated.

15. The composition of claim 1, wherein the at least one synthetic target peptide comprises the amino acid sequence as set forth in SEQ ID NO: 79, wherein the serine at the fourth position is phosphorylated.

16. The composition of claim 1, wherein the at least one synthetic target peptide comprises the amino acid sequence as set forth in SEQ ID NO: 80, wherein the threonine at the third position is phosphorylated.

17. The composition of claim 1, wherein the at least one synthetic target peptide comprises the amino acid sequence as set forth in SEQ ID NO: 84, wherein the serine at the fourth position is phosphorylated.

18. The composition of claim 1, wherein the at least one synthetic target peptide comprises the amino acid sequence as set forth in SEQ ID NO: 87, wherein the serine at the eighth position is phosphorylated.

19. The composition of claim 1, wherein the at least one synthetic target peptide comprises the amino acid sequence as set forth in SEQ ID NO: 93, wherein the serine at the fourth position is phosphorylated.

20. The composition of claim 1, wherein the at least one synthetic target peptide comprises the amino acid sequence as set forth in SEQ ID NO: 94, wherein the serine at the fifth position is phosphorylated.

21. The composition of claim 1, wherein the at least one synthetic target peptide comprises the amino acid sequence as set forth in SEQ ID NO: 97, wherein the serine at the fourth position is phosphorylated.

22. The composition of claim 1, wherein the at least one synthetic target peptide comprises the amino acid sequence as set forth in SEQ ID NO: 99, wherein the serine at the sixth position is phosphorylated.

23. The composition of claim 1, wherein the at least one synthetic target peptide comprises the amino acid sequence as set forth in SEQ ID NO: 100, wherein the serine at the fourth position is phosphorylated.

24. The composition of claim 1, wherein the at least one synthetic target peptide comprises the amino acid sequence as set forth in SEQ ID NO: 101, wherein the serine at the sixth position is phosphorylated.

25. The composition of claim 1, wherein the at least one synthetic target peptide comprises the amino acid sequence as set forth in SEQ ID NO: 102, wherein the serine at the fourth position is phosphorylated.

26. The composition of claim 1, wherein the at least one synthetic target peptide comprises the amino acid sequence as set forth in SEQ ID NO: 104, wherein the serine at the sixth position is phosphorylated.

27. The composition of claim 1, wherein the at least one synthetic target peptide comprises the amino acid sequence as set forth in SEQ ID NO: 105, wherein the serine at the fourth position is phosphorylated.

28. The composition of claim 1, wherein the at least one synthetic target peptide comprises the amino acid sequence as set forth in SEQ ID NO: 110, wherein the serine at the fourth position is phosphorylated.

29. The composition of claim 1, wherein the at least one synthetic target peptide comprises the amino acid sequence as set forth in SEQ ID NO: 112, wherein the serine at the fourth position is phosphorylated.

30. The composition of claim 1, wherein the at least one synthetic target peptide comprises the amino acid sequence as set forth in SEQ ID NO: 113, wherein the serine at the fourth position is phosphorylated.

31. The composition of claim 1, wherein the at least one synthetic target peptide comprises the amino acid sequence as set forth in SEQ ID NO: 114, wherein the serine at the fourth position is phosphorylated.

32. The composition of claim 1, wherein the at least one synthetic target peptide comprises the amino acid sequence as set forth in SEQ ID NO: 115, wherein the serine at the fourth position is phosphorylated.

33. The composition of claim 1, wherein the at least one synthetic target peptide comprises the amino acid sequence as set forth in SEQ ID NO: 117, wherein the serine at the sixth position is phosphorylated.

34. The composition of claim 1, wherein the at least one synthetic target peptide comprises the amino acid sequence as set forth in SEQ ID NO: 118, wherein the serine at the tenth position is phosphorylated.

35. The composition of claim 1, wherein the at least one synthetic target peptide comprises the amino acid sequence as set forth in SEQ ID NO: 120, wherein the threonine at the fourth position is phosphorylated.

36. The composition of claim 1, wherein the at least one synthetic target peptide comprises the amino acid sequence as set forth in SEQ ID NO: 126, wherein the serine at the sixth position is phosphorylated.

37. The composition of claim 1, wherein the at least one synthetic target peptide comprises the amino acid sequence as set forth in SEQ ID NO: 127, wherein the serine at the sixth position is phosphorylated.

38. The composition of claim 1, wherein the at least one synthetic target peptide comprises the amino acid sequence as set forth in SEQ ID NO: 135, wherein the serine at the sixth position is phosphorylated.

39. The composition of claim 1, wherein the at least one synthetic target peptide comprises the amino acid sequence as set forth in SEQ ID NO: 140, wherein the serine at the fourth position is phosphorylated.

40. The composition of claim 1, wherein the at least one synthetic target peptide comprises the amino acid sequence as set forth in SEQ ID NO: 143, wherein the serine at the fourth position is phosphorylated.

41. The composition of claim 1, wherein the at least one synthetic target peptide comprises the amino acid sequence as set forth in SEQ ID NO: 145, wherein the serine at the fourth position is phosphorylated.

42. The composition of claim 1, wherein the at least one synthetic target peptide comprises the amino acid sequence as set forth in SEQ ID NO: 146, wherein the tyrosine at the fifth position is phosphorylated.

43. The composition of claim 1, wherein the at least one synthetic target peptide comprises the amino acid sequence as set forth in SEQ ID NO: 149, wherein the serine at the fourth position is phosphorylated.

44. The composition of claim 1, wherein the at least one synthetic target peptide comprises the amino acid sequence as set forth in SEQ ID NO: 151, wherein the serine at the eighth position is phosphorylated.

45. The composition of claim 1, wherein the at least one synthetic target peptide comprises the amino acid sequence as set forth in SEQ ID NO: 153, wherein the serine at the seventh position is phosphorylated.

46. The composition of claim 1, wherein the at least one synthetic target peptide comprises the amino acid sequence as set forth in SEQ ID NO: 154, wherein the serine at the fifth position is phosphorylated.

47. The composition of claim 1, wherein the at least one synthetic target peptide comprises the amino acid sequence as set forth in SEQ ID NO: 160, wherein the serine at the fourth position is phosphorylated.

48. The composition of claim 1, wherein the at least one synthetic target peptide comprises the amino acid sequence as set forth in SEQ ID NO: 161, wherein the serine at the fourth position is phosphorylated.

49. The composition of claim 1, wherein the at least one synthetic target peptide comprises the amino acid sequence as set forth in SEQ ID NO: 162, wherein the serine at the fourth position is phosphorylated and the serine at the eighth position is phosphorylated.

50. The composition of claim 1, wherein the at least one synthetic target peptide comprises the amino acid sequence as set forth in SEQ ID NO: 163, wherein the serine at the fourth position is phosphorylated.

51. The composition of claim 1, wherein the at least one synthetic target peptide comprises the amino acid sequence as set forth in SEQ ID NO: 166, wherein the serine at the seventh position is phosphorylated.

52. The composition of claim 1, wherein the at least one synthetic target peptide comprises the amino acid sequence as set forth in SEQ ID NO: 167, wherein the serine at the fourth position is phosphorylated.

53. The composition of claim 1, wherein the at least one synthetic target peptide comprises the amino acid sequence as set forth in SEQ ID NO: 168, wherein the serine at the fourth position is phosphorylated.

54. The composition of claim 1, wherein the at least one synthetic target peptide comprises the amino acid sequence as set forth in SEQ ID NO: 169, wherein the serine at the fourth position is phosphorylated.

55. The composition of claim 1, wherein the at least one synthetic target peptide comprises the amino acid sequence as set forth in SEQ ID NO: 170, wherein the serine at the seventh position is phosphorylated.

\* \* \* \* \*